United States Patent [19]

MacLennan

[11] Patent Number: 5,856,443

[45] Date of Patent: *Jan. 5, 1999

[54] MOLECULAR CLONING AND EXPRESSION OF G-PROTEIN COUPLED RECEPTORS

[76] Inventor: Alexander John MacLennan, 7811 NW. 35th Pl., Gainesville, Fla. 32606

[ * ] Notice: The term of this patent shall not extend beyond the expiration date of Pat. No. 5,585,476.

[21] Appl. No.: 760,936

[22] Filed: Dec. 6, 1996

Related U.S. Application Data

[63] Continuation of Ser. No. 196,989, Feb. 15, 1994, Pat. No. 5,585,476.

[51] Int. Cl.$^6$ .......................... C07K 14/705; C12N 15/12
[52] U.S. Cl. ..................... 530/350; 435/69.1; 435/252.3; 435/320.1; 536/23.5
[58] Field of Search ............................... 435/69.1, 252.3, 435/320.1; 530/350; 536/23.5

[56] References Cited

PUBLICATIONS

Yarden, Y. A. Ullrich (1988) "Growth Factor Receptor Tyrosine Kinases" Ann. Rev. Biochem. 57:443–478.
Devreotes, P. (1989) "*Dictyostelium discoideum*: A Model System for Cell–Cell Interactions in Development" Science 245:1054–1058.
Hanley, M.R. (1989) "Mitogenic neurotransmitters" Nature 340:97.
Zachary, I., P.J. Woll, E. Rozengurt (1987) "A Role for Neuropeptides in the Control of Cell Proliferation" Dev. Biol. 124:295–308.
Young, D., G. Waitches, C. Birchmeier, O. Fasano, M. Wigler (1986) "Isolation and Characterization of a New Cellular Oncogene Encoding a Protein with Multiple Potential Transmembrane Domains" Cell 45:711–719.
Gutkind, J.S., E.A. Novotny, M.R. Brann, K.C. Robbins (1991) "Muscarinic acetylcholine receptor subtypes as agonist–dependent oncogenes" Proc. Natl. Acad. Sci. USA 88:4703–4707.
Julius, D., T.J. Livelli, T.M. Jessell, R. Axel (1989) "Ectopic Expression of the Serotonin 1c Receptor and the Triggering of Malignant Transformation" Science 244:1057–1062.
Julius, D., K.N. Huang, T.J. Livelli, R. Axel, T.M. Jesell (1990) "The 5HT2 receptor defines a family of structurally distinct but functionally conserved serotonin receptors" Proc. Natl. Acad. Sci. USA 87:928–932.
MacLennan, A.J., G.D. Frantz, R.C. Weatherwax, N.J.K. Tillakaratne, A.J. Tobin (1990) "Expression of mRNAs That Encode D2 Dopamine Receptor Subtypes: Anatomical, Developmental, and Pharmacological Studies" Molec. Cell. Neurosci. 1:151–160.
Loh, E.Y., J.F. Elliott, S. Cwirla, L.L. Lanier, M.M. Davis (1989) "Polymerase Chain REaction with Single–Sided Specificity: Analysis of T Cell Receptor δ Chain" Science 243:217–220.
Sanger, F., S. Nicklen, A.R. Coulson (1977) "DNA sequencing with chain–terminating inhibitors" Proc. Natl. Acad. Sci. USA 74:5463–5467.
Chirgwin, J.M., E. Przbyla, R.J. MacDonald, W.J. Rutter (1979) "Isolation of Biologically Active Ribonucleic acid from Sources Enriched in Ribonuclease" Biochem. 18:5294–5299.
Okasaki et al. *Biochem. and Biophys. Comm.* 190(3):1104–1109, 15 Feb. 1993.

*Primary Examiner*—John Ulm
*Attorney, Agent, or Firm*—Saliwanchik, Lloyd & Saliwanchik

[57] ABSTRACT

The cloning and expression of two novel rat cDNAs ("H218"and "rat-edg") which encode two members ("$p^{H218}$" and "$p^{rat-edg}$") of the G-protein coupled receptor superfamily of proteins is described. The amino acid sequence similarity between "$p^{H218}$" and "$p^{rat-edg}$" suggests that they may be activated by the same endogenous ligand (s). The expression pattern of mRNA transcripts of both genes in cell lines, various rat tissues and developing rat brain suggests that they both play a role in cell proliferation and/or differentiation. The polynucleotide molecules, proteins, and antibodies of the subject invention can be used in both diagnostic and therapeutic applications.

5 Claims, 12 Drawing Sheets

```
 ..CCCCCCCCCTGAGCCACAGCCAACAGTCACCAAAGTCAGCCACTGGCTGTCCCGG
   GGCGCAGAGCGCCAAGGCCACTCAGGCCAGGACCAGGACCCTGGCCGCCGCCTAGCTGCT
   CAGTCCCATGGCCCCGGCCCGGCCACTGAGCCCCACCATGGCGGTTTATACTCAGAGTAC          8
                                    MetGlyGlyLeuTyrSerGluTyr
```

```
 25  CTCAATCCTGAGAAGGTTCAGGAACACTACAATTACACCAAGGAGACGCTGGACATGCAG        28
     LeuAsnProGluLysValGlnGluHisTyrAsnTyrThrLysGluThrLeuAspMetGln
```

```
 85  GAGACGCCCTCCCGCAAGGTGGCCTCCGCTTCATCATCATTTATGCTGTGCCATCGTG         48
     GluThrProSerArgLysValAlaSerAlaPheIleIleIleIleLeuCysCysAlaIleVal
```

```
145  GTGGAGAACCTTCTGGTGCTAATCGCAGTGGCCAGGAACAGCAAGTTCCACTCAGCCATG        68
     ValGluAsnLeuLeuValLeuIleAlaValAlaArgAsnSerLysPheHisSerAlaMet
```

```
205  TACCTGTTCCTGGCAACCTGGACCTGTCACCCTGTCCTAACTCCCTTGCAGTGGTTTGCCCGA      88
     TyrLeuPheLeuGlyAsnLeuAlaSerAspLeuLeuSerLeuAlaGlyValAlaPheValAla
```

```
265  AACACCTTGCTCTCCGGACCTGTCACCCTGTCCTAACTCCCTTGCAGTGGTTTGCCCGA       108
     AsnThrLeuLeuSerGlyProValThrLeuSerLeuThrProLeuGlnTrpPheAlaArg
```

```
325  GAGGGTTCAGCCTTCATCACGCTCTCTGCCTCTTCAGCCTCCTGGCCATTGCCATC        128
     GluGlySerAlaPheIleThrLeuSerAlaSerValPheSerLeuLeuAlaIleAlaIle
```

```
385  GAGAGACAAGTGGCCATGCCAAGTCAAGCTCTACGGCAGTGACAAAAGCTGTGAATG        148
     GluArgGlnValAlaIleAlaIleAlaLysValLysLeuTyrGlySerAspLysSerCysArgMet
```

```
445  TTGATGCTCATTGGGCCTTCTTGGCTGATATCGCTGATTCTGGTGGCCATCCTG        168
     LeuMetLeuIleGlyAlaSerTrpLeuIleSerLeuIleLeuGlyGlyLeuProIleLeu
```

```
505  GGCTGGAATTGTCTGGACCATCTGGAGGCTTGCTCCACTGTGCCCCTCTATGCTAAG        188
     GlyTrpAsnCysLeuAspHisLeuGluAlaCysSerThrValProLeuTyrAlaLys
```

```
565  CACTATGTGCTCTGCGTGGTCACCATCTTCTGTCATCTTACTGGCTATCGTGGCCTTG       208
     HisTyrValLeuCysValValThrIlePheSerValIleLeuLeuAlaIleValAlaLeu
```

FIG. 1A

625  TACGTCCGAATCTACTTCGTAGTCCGCTCAAGCCATGCGGACGTTGCTGGTCCTCAGACG
     TyrValArgIleTyrPheValValArgSerSerHisAlaAspValAlaGlyProGlnThr   228

685  CTGGCCCTGCTCAAGACAGTCACCACCATCGTACTGGGTGTTTCATCATCTGCTGGCTGCCG
     LeuAlaLeuLeuLysThrValThrIleValLeuGlyValPheIleIleCysTrpLeuPro   248

745  GCTTTTAGCATCCTCTCTTAGACTCTACCTGTCCCGTCCGGGCCTGTCCTGTCCTCTAC
     AlaPheSerIleLeuLeuLeuAspSerThrCysProValArgAlaCysProValLeuTyr   268

805  AAAGCCCATTATTTCTTTGCCTTCGCCACCCTCAACTCTCTGCTCAACCCTGTCATCTAT
     LysAlaHisTyrPhePheAlaPheAlaThrLeuAsnSerLeuLeuAsnProValIleTyr   288

865  ACATGGCGTAGCCGGGACCTTCGGAGGAGGTACTGAGGCGCCCCTGTCTGCTGGGGCAG
     ThrTrpArgSerArgAspLeuArgArgArgGluValLeuArgProLeuLeuCysTrpArgGln   308

925  GGGAAGGAGCAACAGGGCCAGAGGTGGGAACCCTGGTACCGACTCCTGCCCCTCCGC
     GlyLysGlyAlaThrGlyArgArgGlyGlyAsnProGlyHisArgLeuLeuProLeuArg   328

985  AGCTCCAGCTCCCTGGAGAGAGGCTTGCATATGCCTAACATTTCTGAGGC
     SerSerSerSerLeuGluArgGlyLeuHisMetProThrSerProThrPheLeuGluGly   348

1045 AACACAGTGGTCTGAGGGGAAATGTGAACTGATCTGTAACCAAGCCACAGAGAGCTCT
     AspThrValVal                                                   352

FIG. 1B

```
1105 GTGGGGAGAGACCAGTGTGACCTCAGTGTCCCTCAGTGCCACAGGTCTGGAGGAACTGA
1165 CCACGGCTCATAGTCAGTGTGCCAACGGAGGCACTGACTAATCAGATTGTAGTACTGTG
1225 ACTGTGGGGACCATTAAGGGTCTAGGGGACACAGCAGGCTCGAGTTTAGGCTAGACATTT
1285 GCCACTTGGTACATAGGGTGTCGGCATCCTGTCTGTCTTCCAGCTTCCCGGTTCC
1345 CTTCCCTGCCTCCCTCTTTAAGGCCTTCCCAGCCTGGCTAGAGCTTGCTG
1405 TGCAGACCAGCTGACCTGACCCTCCCAGAGATAGATCAACTAACTGTGTCCTGAGTGCT
1465 GGGATTTAAAGCCGTGTGCCCCACAACCCGCTCCTGCCCACCTTCCAGAAGCAATCTTA
1525 GGCCACTGTGAGGAAACTCCACAGCTTCCCAGAGACCCAAGCCTTCTCCCTGTCTCTG
1585 AGGCCTGAATCCACACTGTCCCATTTATCAACTGCTGCTTCCCTTCCCTTCCTCCTTCTGTG
1545 TTCAGGGGAAACCACTGCAGGGAGCGGATCCCCAGTTTTTATGCTCAG
1605 ATCTCACTGAGCACTTGCTTTATGGGAGCAGAGAGAATCAGCTGAGGCAGTGTGGGG
1665 CAGAGTGTGAGGAGAATTTGGGCTTCCTGGTGAGAAACTCTAGGGGAGGCGTTGGTTAT
1725 TCCTGGAACCCAGCCTCTCCCACGAACTCTTCACACCCGCAGCCTTGAGCTGGATGC
1785 AAAGCTGCTTTCAATTTGTCTTTGTTAGTTTTGTTTTGTTTTGTTTTTTTAAATT
1845 GGGACAGATCTCACGTACCCCAGGCTGGCCTCCGACTCACTATGTAGCCAAGGCTGGCT
1905 TTGGACTTCTGACCCTCCTGCCTCCGCTTCTGAGTGCAGGTATTACAAGGGTGTACCAC
1965 CACCACCACCACCAACAACAACAACAACACCTGTCTTGAAACTATCATGA
2025 ATGACAGAGTTCACATAGGTCCTTGGGTGGCCAAGGACATCCCGGATACTCTATGGCATCT
2085 TCCTTGAAGGACTTTGCTAAATCCTGTGGAGAAGTAGAATCCAATACGGTACAAACGG
2145 TGTCTTGAACCTCTTATGTGCACATCCGTGTCAAGACTGCTAGAGACTGCTATCCCAGTGTGGTGC
2205 TGTCTCTGACCTCTTATGTGCACATCCGTGTCAAGACTGCTAGAGAGATGGACGGGGGTGTG
2265 TGTGCTTGTGGGGTCTAGCCATGCTGAGCTAGCAGCCTGGAATTGCTGAATCATCTCCC
2325 ACACACAGACACACACCTCCGCTTAAAGAATGTGAAAGAAAAGCTGAGGAAGGGG
2385 AGATTTGGAGGCAGTCGGGAGCCAGTGTCTCCCATACAGCTTCCATATG
2445 TCCCCCTTGTCTGGAAACCCAGAACTGGGCCAATAAACAGTTCAATTTCTCTTGAAAAA
2505 AAA
```

```
                                                                                           TMD#1
pH218   MG........GLYSEYINPEKVQEHYNYTKETLDMQETPSR..KVASAFIIITCCAIVENLIVLIAVERN.SKFH
D2      MD....PL..NLSWYDDDLERQNWSRPFNGSEGKADRPHYNYYAMLLTLLI.FI.IVFGNVLVCMAVSREKALQT
β2      MGP...P...GNDSDFLLTTNGSHV...PDHDVTEERDEAWVGMAILMSVIVL.AIVFGNVLVITAIAKFERLQT
α2      MGSLQ.PDA.GNASWNGTEAPG..GGARATPYSLQVT...LTLVCLAGLL.MLLT.VFGNVLVIIAVFTSRALKA
5HT1A   MDVLS.PGO.GNNTTS...PPAPFETGGNTTGISDVTVSYQV.ITSLLLGTL.IFC.A.VLGNACVVAAIALERSLQN
M1      MNTSAPPAVSPNIT.VIAPGKGPWQVA...............FIGITTGLLSL.AT.VTGNLLVIVSFKVNTELKT
SK      MGACV.VMTDINISSGL........DSNATGITAFSMPGWQLALWTIAYLALVL.VA.VMGNATMIWILLAHQRMRT

TMD#2
        SAMVLFGNIAASDIIAGVA....FVANTLLSGPVTLSLT
        TTNYI..IVSIAVADLIVATLVMPWVVYLEVVCEWKFS...
        VTNY..FITSLACADLVMGLAVVPFGASHILMKMWNFG...
        PQN..IFLTSLASADILVATLVIPFSLANEVMGYWYFG..
        VANYI..IGSILVTDLMVSVLVLPMAALYQVLNKWTLG..
        VNNY..FLLSLACADLILGTFSMNLYTTYLLMGHWALG..
        VTNY..FIVNLALADLCMAAFNAAFNFVYASHNIWYFG..
           TMD#2

TMD#4
pH218   PLQWFAREGS.AFITTLS..ASVFSLLATAIERQVATAKVKLYGSDKS..CRMLMLGASWLISLILGGLPIL.GWN
D2      .RIH..CDIFVTLDVMCTASILNLCAISIDRYTAVAMPLYNTRYSSKRRVTVMIAIVWVLSFTISC.PLLFGLN
β2      .NFW..CEFWTSIDVLCVTASIETLCVIAVDRYIATLSPFKYQSLLTKNKAR.MVLMVWIVSGLTSFLPIQMHWY
α2      .KIW..CEIYLALDVLFCTSSIVHLCAISLDRYWSITQAIEYN.LKRTPRRIKAIIITVVVISAVISFPPLLISIEK
5HT1A   .QVT..CDLFIALDVLCCTSSILHLCATALDRYWATTDPIDYVNKRTPRRAT.SLT.WLIGFLISIPPMLGWRT
M1      .TLA..CDLWLALDYVASNASVMNLLLISFDRYFSVTRPLSYRAKRTPRRAAAIM.IGLAWLVSFVLWA.PAILFWQ
SK      .RAF..CYFQNLFPITAMFVSIYSMTAIAADRYMAIVHPFQPRL.SAPGTR.AV.IAGIMLVALALAF.PQCFYST

TMD#5
        CLDHLEACST...VLPLYAKHYVLCVVTFSVLLAIVA
        NTDQNE.........CIIANPAFVVYSSIVSFYVPFIVT
        RATHQKA..IDCYHRETCCDFFTNQAYAIASSIVSFYVP
        KGGGGPQ.....PAEPRCEINDQKWYVISSCIGSFFAP
        PEDRSDPDA.....CTISKDMGYTIYSTFGAFYIP
        YLVGE....RTVLAGQCYIQFLSQPIIFGTAMAAFYLP
        ITTDEGATKCVVAWPEDSGGKMLLYHLIVIALIYF.LP
```

FIG. 2B

```
                         TMD#6
P^H218  LYV..RIYFVRSSHADVAGP.......QTLALLKTVTIVLGVFIICWLPAFSILEDSTCPVRACPVLY
D2      LLVYIKIYIVLRKRKRVNTK-(112)--KEKKATQMLAIVLGVFIICWLPFFITHILNIHC...DCNI.P
β2      LVVMVFVYSRVFQVAKRQLQK-(33)---KEHKALKTLGIIMGIFTLCWLPFFIVNIVHVI...QDNLI.P
α2      CLIMILVRIYQIAKRRTRV-(138)----REKRFTFVLAVIGVFVVCWFPFFFTYTLTAV....GCSV.P
5HT1A   ELLMLVLGRIFRAARFRIPK-(111)---RERKTVKTLGIIMGTFILCWLPFFIVALVLPFCE.SSCHM.P
M1      VTVMCTLYWRIYRETENRARE-(138)--KEKKAARTLSAILLAFIVTWTPYNIMVLVSTFC...KDC.P
SK      LVVMFVAYSVIGLTLWRRSVP-(13)---AKKKFVKIMVLVVTFEAICWLPYHLYFILGTFQEDIYCHKFI

TMD#7
P^H218  KAHY..FFAFATLNSLLNPVIYTWRSRDLRREVLRPELC---(46)
D2      PVLYSAFTWLGYVNSAVNPIIYTTFNIEFRKAFMKILHC
β2      KEVYILLNWLGYVNSAFNPLIYC.RSPDFRIAFQELL..C---(37)
α2      RTLFKFFWFGYCNSSLNPVIYTIFNHDFRRAFKKIL..C---(8)
5HT1A   TLLGAIINWLGYSNSLLNPVIYAYFNKDFQNAFKKIIKC---(5)
M1      ETLWELGYWLCYVNSTINPMCYALCNKAFRDTFRLLLLC---(25)
SK      QQVYLALFWLAMSSTMYNPIIYCCLNHRFRSGFRLAFRC---(63)
```

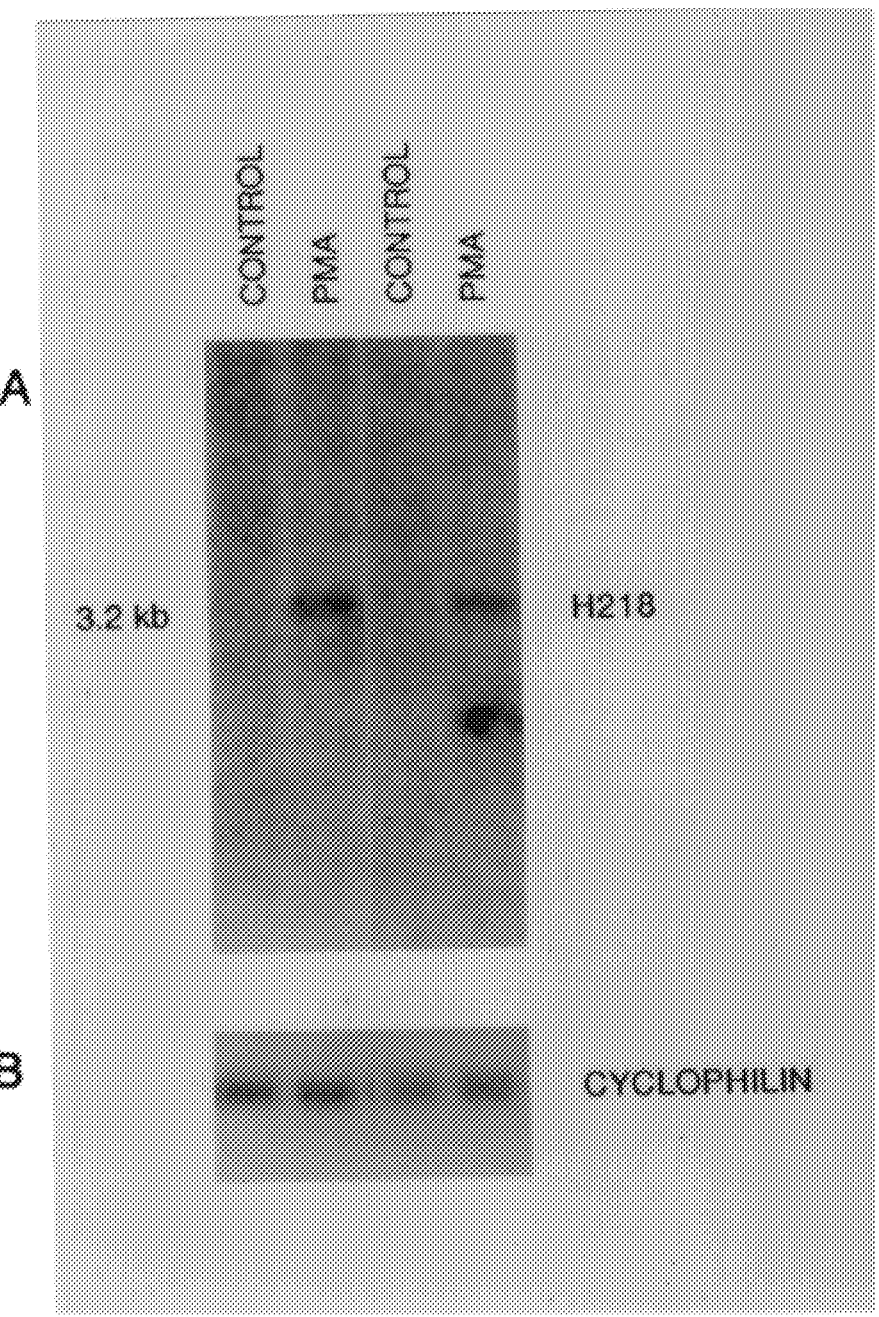

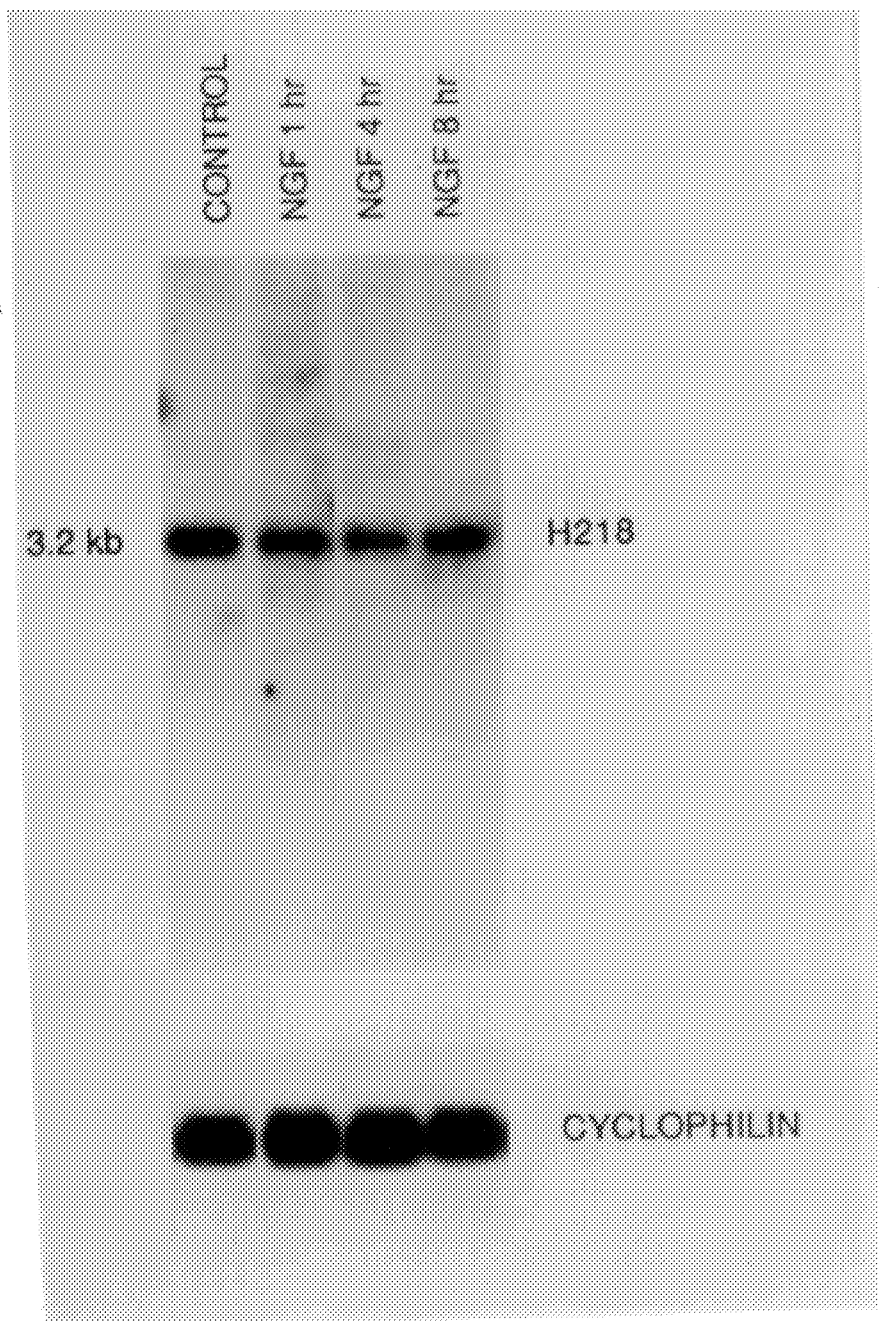

```
-260         TTTGCTGGTCTCCGTCAGTCGCCGACAGCAGCAAGATGCGGATCGCGCGGTGTAG
-206 ACCCGGAGCCCGGCGGACGCAGCTTCGTCCGCTTGAGCGAGGCTGCTGTTTCTCGGAGG
-146 CCTCTCCAGCCAAGGAGAAAACTACATAAAAAGCATCGGATTGCTTGCTGACCTGGCCTT
 -86 GCTGTAACTGAAGGCTCGCTCAACCTGCCCCTCTAGCGTTTGTCTGGAGAAGTACCACCC
 -26 CGGGCTCCTGGGACACAGTTGCGCTATGGTCCTCCACCAGCATCCCAGTGGTTAAG
                            MetValSerSerThrSerIleProValValLys    11

34 GCTCTCCGCAGCCAAGTCTCCGACTATGGCAACTATGATATACATGTCCGGCATTACAAC
     AlaLeuArgSerGlnValSerAspTyrGlyAsnTyrAspIleIleValArgHisTyrAsn 31

94 TACACAGGCAAGCTGAACATCGGAGTGGAGAAGGACCATTGGCATTAAACTGACTTCAGTG
     TyrThrGlyLysLeuAsnIleGlyValGluLysAspHisGlyIleIleLysLeuThrSerVal 51

154 GTGTTCATTCTCATCTGCTGCTTGATCATCCTAGAGAATATATTTGTCTGCTAACTATT
     ValPheIleLeuIleLeuCysCysLeuIleLeuIleLeuGluAsnIlePheValLeuThrIle 71

214 TGGAAAACCAAGAAGTTCCACGGCCCATGTACTATTCATAGGCAACCTAGCCCTCTCG
     TrpLysThrLysPheHisArgProMetTyrTyrPheIleGlyAsnLeuAlaLeuSer 91

274 GACCTGTTAGCAGGAGTGGCTTACACAGCTTACACAGCTGCTGTTGTCTGGGGCCACCACCTAC
     AspLeuLeuAlaGlyValAlaTyrThrAlaAsnLeuLeuLeuSerGlyAlaThrThrTyr 111

334 AAGCTCACACCTGCCCAGTGGTTTCTGCGGGAAGAAGTATGTTTGTGGCTCTGTCTGCC
     LysLeuThrProAlaGlnTrpPheLeuArgGluGlySerMetPheValAlaLeuSerAla 131

394 TCAGTCTTCAGCCTCCTTGCTATCGCCATTGAGCGCTACATCACCATGCTGAAGATGAAA
     SerValPheSerLeuLeuAlaIleAlaIleGluArgTyrIleThrMetLeuLysMetLys 151

454 CTACACAACGGCAGCAACAGCTCGCGCTCCTTTCGCTGATCAGTCGCCTGCTGGGTCATC
     LeuHisAsnGlySerAsnSerSerArgSerPheLeuLeuIleSerAlaCysTrpValIle 171
```

FIG. 7A

514   TCCCTCATCCTGGGTGGGCTGCCATCATGGGCTGGAACTGCATCAGCTCGCTGTCCAGC
      SerLeuIleLeuGlyGlyLeuProIleMetGlyTrpAsnCysIleSerSerLeuSerSer 191

594   TGCTCCACCGTGCTCCCGCTCTACCACAAGCACTATATTCTCTTCTGCACCACCGTCTTC
      CysSerThrValLeuProLeuTyrHisLysHisTyrIleLeuPheCysThrThrValPhe 211

654   ACCCTGCTCCTGCTTCCATCGTCTACTCCTCTGCAGGATCTACTCCTTGGTGAGGACT
      ThrLeuLeuLeuSerIleValIleLeuTyrCysArgIleTyrSerLeuValArgThr 231

714   CGAAGCCGCCTGACCTTCCGCAAGAACATCTCCAAGGCCAGCCGCAGTTCCGAGAAG
      ArgSerArgArgLeuThrPheArgLysAsnIleSerLysAlaSerArgSerGluLys 251

774   TCTCTGGCCTTGCTGAAGACAGTGATCATTGTCCTGAGTGTCTTCATTGCCTGCTGGCC
      SerLeuAlaLeuLeuLysThrValIleIleValLeuSerValPheIleAlaCysTrpAla 271

834   CCTCTCTTCATCCTACTACTTTTAGATGTGGGGTGCAAGGCGAAGACCTGTGACATCCTG
      ProLeuPheIleLeuLeuLeuLeuAspValGlyCysLysAlaLysThrCysAspIleLeu 291

894   TACAAAGCAGAGTACTTCCTGGTTCTCGCTGTGAACTCAGGTACCAACCCCATCATC
      TyrLysAlaGluTyrPheLeuValLeuAlaValLeuAsnSerGlyThrAsnProIleIle 311

954   TACACTCTGACCAATAAGGAGATGCGCCGGGCCTTCATCAGATCATATCTTGTTGCAAA
      TyrThrLeuThrAsnLysGluMetArgArgAlaPheIleArgIleIleSerCysCysLys 331

1114  TGCCCCAACGGAGACTCCGCTGCAAATTCAAGAGGCCCATCATCCCGGGCATGGAATTT
      CysProAsnGlyAspSerAlaGlyLysPheLysArgProIleIleProGlyMetGluPhe 351

1194  AGCCGCAGCAAATCAGACAACTCCTCCCACCCCAGAAGGATGATGGGACAATCCAGAG
      SerArgSerLysSerAspAsnSerSerHisProGlnLysAspAsnProGlu 371

1254  ACCATTATGTCTTCTGAAACGTCAATTCTTCTTCTTAAAACCGGAAGCTGTTGATACTG
      ThrIleMetSerSerGlyAsnValAsnSerSer*** 383

FIG. 7B

```
1314 TTGATTCTGGCTTCATCACTCACTCCCTAGCATTTCAAAAACATCTCTCTTTCTCCACT
1374 GCTGCAAGGAAGAAGCAGCCGGGAGCCTGAGAGAGGGAAGGGAGGAGAATGTGCGGCTT
1434 GGTGATACCATGTTGTAGGTAGGTTATGATTATGAACAATGCCCTGGGAAGGGTGGAGAT
1494 CAGATCTGCCCTGCAGAGGGTTTCCTGCCCCTAATCTCTCTCACTTCCTTCCTTCAGTCGTT
1554 TCTGTTTATCCCCATACTCTTTTTTTCTTCCGTTTTCTCATTCCCCTTCTCTACC
1614 ATCGCTTTCTTTTCTTCTTTAAATTTAGGGGCAACAAAGGAATCCCACAAATGGA
1674 TATTGTGAAACATAGTGCTGAATGACGGGCAAAGATGGTAAATCAAAAGATAAAT
1734 TAACTTCATAAGACTGCTATTCTGAAATGCAACAATCTTGTACAGTCAGACTGATAAAA
1794 TGGAGCAATCAGACATTTCAGACACAAAATCACCTACTTGAACAATACTTGAACATTGTAT
1854 GCAATACATTCACACAAAAGCAAATACTGTAGCCTTATTTGAACAATACTGAACTCAT
1914 AAATACTCATGGTTTCACTCGTTCCAGGCGCCTAAGGACTATGCTGCTGTAATACAGGAA
1974 AACACAGCGGATGCCTCCTATTAAAATGTCACTCAAGAAAAGTCTCTTGTAACGTAAA
2034 GGCAAACACATGTAGCTACTGAGCTACTGACGTCCTTGGTCACACTCTATGGGAAAAACA
2094 CCGGACTCCAC
```

FIG. 7C

MOLECULAR CLONING AND EXPRESSION OF G-PROTEIN COUPLED RECEPTORS

This is a continuation of application Ser. No. 08/196,989, filed Feb. 15, 1994 now U.S. Pat No. 5,585,476.

This invention was made with government support under the National Institute on Drug Abuse grant number DA07244. The government has certain rights in this invention.

BACKGROUND OF THE INVENTION

The development of multicellular organisms requires the orchestration of many precisely coordinated events involving cell-type specific growth, proliferation, differentiation, migration, and cell death. Not surprisingly, intercellular communication plays critical roles in these processes. Although the molecular mechanisms involved in this communication are in general poorly understood, this research field is characterized by increasingly rapid progress initiated by the realization that viral oncogenes are, in many cases, transformed versions of cellular genes (proto-oncogenes) that participate in the intercellular communication directing development. Furthermore, it has been established that many non-viral forms of cancer also result from transformation of genes involved in signal transduction (e.g. growth factors, growth factor receptors, and transcription factors).

A large number of mammalian growth factor receptors have been cloned and many are recognized proto-oncogenes (Yarden and Ullrich, 1988). Most of these cloned receptors are members of a superfamily of integral membrane proteins with intrinsic, growth factor-inducible, tyrosine kinase activity. An extensive research literature now documents the critical roles these receptors play in cell proliferation, differentiation, and malignant transformation. However, multiple lines of evidence suggest that members of the G-protein coupled receptor (GPR) superfamily may also participate in mammalian development and oncogenesis. For example, both the yeast S. cerevisiae and the slime mold D. discoideum express GPRs that regulate cell differentiation (Devreotes, 1989; Sprague, 1991). In addition, mammalian mitogenesis and cell proliferation are affected by several peptides and neurotransmitters which are known to interact with GPRs (Hanley, 1989; Zachary et al., 1987).

Perhaps the most direct evidence linking GPRs with ontogeny and cancer has been provided by the ectopic expression of GPRs in tissue culture cells. Thus, the mas oncogene encodes a putative GPR ($p^{mas}$) and leads to malignant transformation when transfected into NIH3T3 mouse fibroblasts cells (Young et al., 1986). In addition, several serotonin and muscarinic acetylcholine receptors (all GPRs) also produce this malignant transformation if ectopically expressed in NIH3T3 cells and stimulated by their respective ligands (Gutkind et al., 1991; Julius et al., 1989; Julius et al., 1990). While these data illustrate that GPRs can greatly influence cell proliferation and morphology, the GPRs that were studied are unlikely to be involved in these processes in vivo because they reside in fully differentiated, postmitotic cells such as neurons where serotonergic receptors, muscarinic receptors, and most likely $p^{mas}$ regulate the changing electrical properties of neuronal membranes involved in neurotransmission. However, these data support the possibility that other GPRs are expressed in vivo in immature cells where they regulate proliferation and differentiation. Furthermore, these data suggest that some forms of cancer may result from mutations or viral infections that lead to improper functioning, activation, or expression of such GPRs. Thus, identification and characterization of such receptors should significantly advance both the study of normal development as well as the search for diagnostic and therapeutic tools in oncology.

BRIEF SUMMARY OF THE INVENTION

The subject invention concerns the cloning and sequencing of cDNAs and the proteins encoded by those cDNAs. The cDNAs encode novel polypeptides that are members of the G-protein coupled receptor (GPR) superfamily. The proteins encoded by the DNAs of the subject invention are involved in the regulation of cell proliferation and/or differentiation in vivo. The subject protein receptors are endogenously expressed in various tissues and cell lines.

Specifically, the subject invention concerns the cloning and sequencing of a rat cDNA (H218) that encodes a novel GPR designated $p^{H218}$. Further included in the subject invention are mammalian homologs, including the human homolog of the H218 cDNA. The H218 cDNA was used to determine that H218 mRNA is expressed in all developing organs tested and in seven out of seven cell lines tested. In addition, in the brain, H218 mRNA is much more highly expressed during a period of extensive proliferation and differentiation (embryogenesis) than a period of very limited cell proliferation and differentiation (adulthood), suggesting that $p^{H218}$ does not function as a neurotransmitter receptor. Rather, $p^{H218}$ functions as a growth factor ligand receptor.

The subject invention further concerns antibodies from animals immunized with peptides derived from $p^{H218}$ GPR. Purified antibody made against one of the peptides recognizes a protein having an apparent molecular weight of 50–55 kDA as determined by Western blot analysis.

The subject invention also concerns cDNA of the rat-edg gene. Rat-edg cDNA encodes a GPR, $p^{rat-edg}$. The $p^{rat-edg}$ can be activated by some of the same ligand(s) that activate $p^{H218}$. By identifying compounds that specifically activate or inhibit this class of receptors one can develop unique, pharmaceutical therapies that effectively treat some forms of cancer.

A further aspect of the subject invention concerns polynucleotide molecules that are antisense to mRNA of H218 and rat-edg. The antisense polynucleotide molecules can be used to reduce or inhibit the expression of the subject protein by binding to the complementary mRNA transcripts.

The subject invention also concerns methods of use for the polynucleotide sequences, the encoded proteins, peptide fragments thereof, polynucleotide molecules that are antisense to the H218 and rat-edg sequences, and antibodies that bind to the proteins and peptides. Such use includes diagnostic and therapeutic applications of the subject invention.

BRIEF DESCRIPTION OF THE DRAWINGS

FIG. 1 shows the nucleotide and deduced amino acid sequence of H218 cDNA. The sequence was compiled from that of "H2" cDNA (nucleotides 16 to 2505) and "18" cDNA (nucleotides −155 to 288) which are identical throughout the region of overlap. A black box highlights the optimal consensus sequence for translation initiation. A potential polyadenylation signal is double-underlined and a consensus sequence associated with mRNA instability is boxed. Repetitive nucleic acid sequences in the 3' untranslated region are underlined. An arrow designates a predicted N-glycosylation site. A consensus sequence for proline directed kinases is underlined with a broken line. Brackets below the amino acid sequence indicate possible nucleotide binding site components in the carboxy-terminal and "third cytoplasmic loop" domains respectively.

FIG. 2 shows a comparison of $p^{H218}$ with other G-protein coupled receptors. Black boxes highlight residues identical to $p^{H218}$ residues. D2=D2 dopaminergic receptor; β2=β2 adrenergic receptor; α2=α2 adrenergic receptor; 5HT1A=1A serotonergic receptor; M1=M1 muscarinic receptor; SK=substance K receptor. The numbers in parentheses indicate the number of omitted residues.

FIG. 5 shows an X-ray autoradiograph of a Northern blot illustrating the effect of PMA treatment on H218 mRNA levels in RJK88 fibroblasts. Poly-A RNA was extracted from 2 independent 100 mm plates of cells treated with PMA for 2 hrs (PMA) or 2 parallel plates of cells treated with vehicle (CONTROL). The resulting blot was probed for H218 mRNA (panel A), stripped, and then probed for cyclophilin mRNA (panel B) as an extraction, loading, and transfer control. Lanes are presented in pairs based on their relative mRNA content (as indicated by the cyclophilin data).

FIG. 6 shows an X-ray autoradiograph of a Northern blot illustrating the effect of NGF treatment on H218 mRNA levels in PC12 cells. Poly-A RNA was extracted from 4 independent 100 mm plates of cells treated with NGF for either 1, 4, or 8 hrs or with a vehicle (CONTROL). The blot was probed for H218 mRNA (panel A), stripped, and then probed for cyclophilin mRNA (panel B) as an extraction, loading, and transfer control.

FIG. 7 shows the nucleotide and deduced amino acid sequence of rat-edg cDNA. An ATTA motif is boxed in black.

BRIEF DESCRIPTION OF THE SEQUENCES

Figures 3A, 3B:
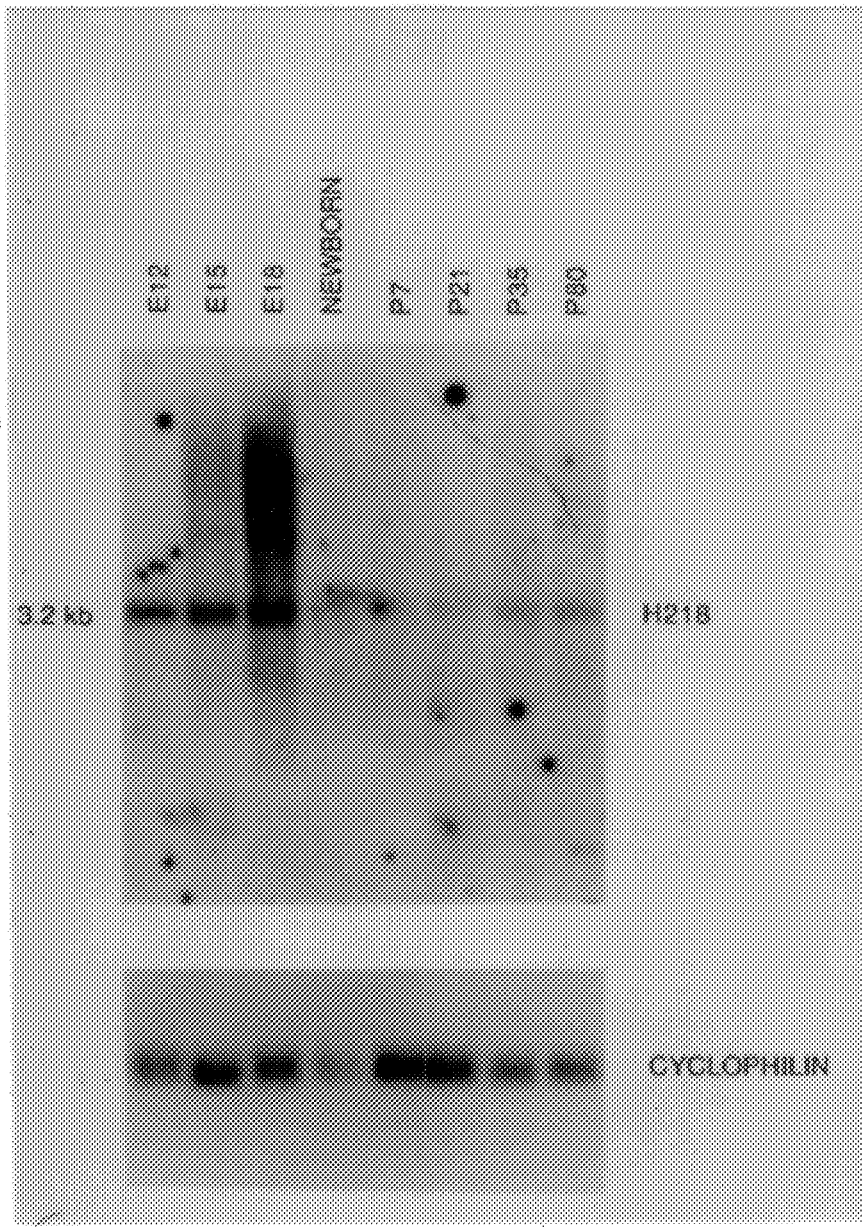
FIG. 3 shows an X-ray autoradiograph of a Northern blot illustrating the ontogenic regulation of H218 mRNA levels in the rat brain. Poly-A RNA was extracted from whole rat brain at embryonic days 12, 15, 18, Birth, postnatal days 7, 21, 35, and 80 (adult). The resulting blot was probed for H218 mRNA (panel A), stripped, and then probed with a cyclophilin cDNA (panel B) to control for variation in extraction, loading, and transfer (brain cyclophilin mRNA levels are reported to be stable from E12 to adult). The relative intensity of the cyclophilin bands have consistently paralleled results obtained from probing the same blots with an oligo-dT probe designed to hybridize to all mRNA poly-A tails.

SEQ ID NO.1 is the nucleotide sequence of the $^{H218}$ cDNA.

SEQ ID NO.2 is the deduced amino acid sequence of the $p^{H218}$ protein encoded by the H218 cDNA.

SEQ ID NO.3 is the nucleotide sequence of the rat-edg cDNA.

SEQ ID NO.4 is the deduced amino acid sequence of the $p^{rat-edg}$ protein encoded by the rat-edg cDNA SEQ ID NO.5 is the amino acid sequence of a synthetic $p^{H218}$ peptide designated peptide 1.

SEQ ID NO.6 is the amino acid sequence of a synthetic $p^{H218}$ peptide designated peptide 2.

SEQ ID NO.7 is the amino acid sequence of a synthetic pH218 peptide designated peptide 3.

SEQ ID NO.8 is the amino acid sequence of a synthetic $p^{H218}$ peptide designated peptide 4.

SEQ ID NO.9 is the amino acid sequence of a D2 dopaminergic receptor.

SEQ ID NO.10 is the amino acid sequence of a β2 adrenergic receptor.

SEQ ID NO.11 is the amino acid sequence of a α2 adrenergic receptor.

SEQ ID NO.12 is the amino acid sequence of a 1A serotonergic receptor.

SEQ ID NO.13 is the amino acid sequence of a M1 muscarinic receptor.

SEQ ID NO.14 is the amino acid sequence of a substance K receptor.

Detailed Disclosure of the Invention

The subject invention concerns novel cDNAs (H218 and rat-edg) that encode G-protein coupled receptors. The proteins, designated $p^{H218}$ and $p^{rat-edg}$, play important roles in cell proliferation and differentiation, and in disease states such as cancer.

The H218 cDNA has been sequenced (SEQ ID NO.1) and the amino acid sequence of the polypeptide that it encodes determined (SEQ ID NO.2) (FIG. 1). The H218 cDNA contains a 1056 bp open reading frame that encodes a polypeptide of 352 amino acids. The 3' untranslated region of H218 cDNA contains repetitive sequences, a consensus sequence for mRNA instability, and a series of terminal adenosines preceded by a potential polyadenylation site. The predicted cytoplasmic regions of pH218 contain potential nucleotide binding site components and a consensus sequence for proline directed kinases involved in cell division and growth factor responses.

Analysis of the deduced amino acid sequence of $p^{H218}$ revealed that it is a member of the GPR superfamily (FIG. 2). Several features of $p^{H218}$ are common to all other GPRs, including: 1) seven regions of hydrophobicity which are predicted to act as membrane spanning domains, 2) a consensus sequence for N-linked glycosylation in its predicted N-terminal extracellular domain, and 3) a conserved cysteine residue and several serine and threonine residues in its predicted intracellular C-terminal domain. In addition, $p^{H218}$ contains many other residues which are highly conserved among most GPRs. However, $p^{H218}$ is distinct from these GPRs in that it does not contain certain highly conserved residues. Perhaps most notable are the aspartate and tyrosine residues at the cytoplasmic end of the third transmembrane domain, and the cysteine residue at the extracellular end of the same transmembrane domain.

$p^{H218}$ affects the course of cellular proliferation and/or differentiation events. Of all cloned proteins, $p^{H218}$ is most homologous to human $p^{edg}$, a putative GPR implicated in endothelial cell differentiation. The possibility of a direct interaction between $p^{H218}$ and growth-related intracellular proteins is suggested by the similarity between the predicted cytoplasmic region of $p^{H218}$ and motifs of the src homology domain 2 (SH2) found in many cytoplasmic proteins that are critically involved in growth-related signal transduction, including several proteins encoded by oncogenes.

A further aspect of the subject invention concerns polynucleotide molecules which encode the human homolog of the rat H218 gene. Human cDNAs that hybridize with H218 cDNA were isolated from a human embryonic brain cDNA library. These polynucleotide molecules can be used to express the human counterpart of $p^{H218}$. Antibodies can then be raised against the expressed protein, or peptide fragments thereof. The polynucleotide molecules, proteins, and antibodies of the human homolog of $p^{H218}$ can be used in both diagnostic and therapeutic applications.

A further aspect of the subject invention concerns antibodies raised against synthetic peptides of $p^{H218}$. These peptides, designated as 1, 2, 3, and 4 (and corresponding to SEQ ID NO.5, SEQ ID NO.6, SEQ ID NO.7, and SEQ ID NO.8, respectively), correspond to separate extracellular and intracellular regions of $p^{H218}$. These peptides and their amino acid sequence are shown in Table 1.

TABLE 1

Amino Acid Sequences of $p^{H218}$ peptides

| $p^{H218}$ peptide | | Sequence |
| --- | --- | --- |
| peptide 1 | SEQ ID NO. 5 | KETLDMQETPSR |
| peptide 2 | SEQ ID NO. 6 | YSEYLNPEKVQE |
| peptide 3 | SEQ ID NO. 7 | RQGKGATGRRGG |
| peptide 4 | SEQ ID NO. 8 | RSSSSLERGLHM |

Polyclonal antibodies that react with the antigen peptides were raised in rabbits immunized with the respective peptide. Each antibody recognizes by an ELISA assay the specific peptide used as the immunogen. One of the antibodies, from a rabbit immunized with peptide 1 (SEQ ID NO.5), was affinity purified and used in a Western blot with antigens from a cell line that expresses H218 mRNA This antibody recognized a band of 50 to 55 kDa, and a band of 180 to 200 kDa in the Western blot. These antibodies can be used for detecting and purifying the $p^{H218}$ protein through standard procedures known in the art. The antibodies can also be used for localization of $p^{H218}$ in tissues using immunohistochemical techniques known in the art.

The subject invention further contemplates the use of the protein and peptides to generate both polyclonal and monoclonal antibodies. Thus, monoclonal antibodies to $p^{H218,}$ and peptide fragments thereof, can be produced using the teachings provided herein in combination with procedures that are well known in the art. Such antibodies can be produced in several host systems, including mouse, rat, and human.

Also included within the scope of the invention are binding fragments of the antibodies of the subject invention. Fab; F(ab')$_2$, and Fv fragments may be obtained by conventional techniques, such as proteolytic digestion of the antibodies by papain or pepsin, or through standard genetic engineering techniques using polynucleotide sequences that encode binding fragments of the antibodies of the subject invention.

A further aspect of the subject invention concerns the cloning and sequencing of the rat homolog of the human edg gene, which also encodes a GPR. This rat gene, designated rat-edg, is similar in sequence to the human edg gene. The rat-edg cDNA (SEQ ID NO.3) encodes a protein, $p^{rat-edg}$ (SEQ ID NO.4). The $p^{rat-edg}$ protein also has several features in common with other members of the GPR superfamily including 1) seven hydrophobic regions presumed to act as transmembrane domains, 2) a putative N-glycosylation site in the N-terminal domain, 3) putative phosphorylation sites in cytoplasmic domains, and 4) a conserved cysteine residue in the C-terminal domain.

The subject invention also concerns polynucleotide molecules having sequences that are antisense to mRNA transcripts of H218 and rat-edg polynucleotides. An administration of an antisense polynucleotide molecule can block the production of the protein encoded by H218 or rat-edg.

The techniques for preparing antisense polynucleotide molecules, and administering such molecules are known in the art. For example, antisense polynucleotide molecules can be encapsulated into liposomes for fusion with cells.

As is well known in the art, the genetic code is redundant in that certain amino acids are coded for by more than one nucleotide triplet (codon). The subject invention includes those polynucleotide sequences which encode the same amino acids using a different codon from that specifically exemplified in the sequences herein. Such a polynucleotide sequence is referred to herein as an "equivalent" polynucleotide sequence. Thus, the scope of the subject invention includes not only the specific polynucleotide sequences depicted herein, but also all equivalent polynucleotide sequences encoding the polypeptides of the subject invention, and fragments or variants thereof.

The polynucleotide sequences of the subject invention can be prepared according to the teachings contained herein, or by synthesis of oligonucleotide fragments, for example by using a "gene machine" using procedures well known in the art.

The polypeptides of the subject invention can be prepared by expression of the cDNAs in a compatible host cell using an expression vector containing the polynucleotide sequences of the subject invention. The polypeptides can then be purified from the host cell using standard purification techniques that are well known in the art. Alternatively, the polypeptides of the subject invention can be chemically synthesized using solid phase peptide synthesis techniques known in the art.

The polypeptides of the subject invention can be used as molecular weight markers, as an immunogen for generating antibodies, and as an inert protein in certain assays. The polynucleotide molecules of the subject invention can be used as DNA molecular weight markers, as a chromosome marker, and as a marker for the gene on the chromosome.

The term "polynucleotide sequences" when used in reference to the subject invention can include all or a portion of the cDNA. Similarly, polynucleotide sequences of the subject invention also includes variants, including allelic variations or polymorphisms of the genes. The polynucleotide sequences of the invention may be composed of either RNA or DNA. More preferably, the polynucleotide sequences of the subject invention are composed of DNA.

As used herein, the term "isolated" means, in the case of polynucleotide sequences, that the sequence is no longer linked or associated with other polynucleotide sequences with which it would naturally occur. Thus, the claimed polynucleotide sequences can be inserted into a plasmid or other vector, to form a recombinant DNA cloning vector. The cloning vector may be of bacterial or viral origin. The vector may be designed for the expression of the polypeptide encoded by the polynucleotide sequence. The vector may be transformed or transfected or otherwise inserted into a host cell. The host cell may be either prokaryotic or eukaryotic, and would include bacteria, yeast, insect cells, and mammalian cells. For example, a bacterial host cell may be *E. coli*, and a mammalian host cell may be the PC12 cell line.

As used herein, the term "isolated" means, in the case of proteins, obtaining the protein in a form other than that which occurs in nature. This may be, for example, obtaining $p^{H218}$ by purifying and recovering the protein from a host cell transformed to express the recombinant protein. In the case of antibodies, "isolated" refers to antibodies, which, through the hand of man, have been produced or removed from their natural setting. Thus, isolated antibodies of the subject invention would include antibodies raised as the result of purposeful administration of the proteins, or peptide fragments thereof, of the subject invention in an appropriate host.

The various genetic engineering methods employed herein are well known in the art, and are described in Sambrook, J., et al (1989) *Molecular Cloning: A Laboratory Manual*, Cold Spring Harbor Laboratory, New York. Thus, it is within the skill of those in the genetic engineering art to screen cDNA libraries, perform restriction enzyme digestions, electrophorese DNA fragments, tail and anneal vector and insert DNA, ligate DNA, transform or transfect host cells, prepare vector DNA, electrophorese proteins, sequence DNA, perform Northern, Southern and Western blotting, and perform PCR techniques.

MATERIALS AND METHODS

Cloning of H218 cDNA.

A "LAMBDA ZAP" cDNA library (Stratagene, La Jolla, Calif.) constructed using rat hippocampal RNA was screened at medium stringency with a 926 bp 5' EcoRI-Bgl II 3' fragment of a D2 dopamine receptor cDNA (MacLennan et al., 1990). The cDNA was labeled with $^{32}P$ by random hexamer priming. Nitrocellulose filters were incubated for 2 hrs at 42° C. in 5X SSPE (1X SSPE=0.15M NaCl, 12 mM $NaH_2PO_4$•H20, 1 mM EDTA, pH 7.4), 40% formamide, 0.15% SDS, 5X Denhardt's solution, 100 μg/ml denatured salmon sperm DNA, and 2 μg/ml polyadenylic acid. The filters were then incubated overnight in the same solution at 42° C. with the probe added (approximately $10^6$ cpm/ml). The filters were washed two times for 15 minutes each at room temperature in 2X SSC (standard saline citrate buffer: 1X SSC=0.15M NaCl, 0.015M sodium citrate, pH 7.2), followed by two washes for 45 minutes each at 42° C. in 2X SSC.

In order to exclude D2 receptor cDNAs from analysis, all hybridizing phage were screened at high stringency with four oligodeoxynucleotide probes designed to specifically recognize D2 dopamine receptor cDNAs (MacLennan et al., 1990). All phage that hybridized to the oligonucleotides were eliminated from further rounds of purification. All other phage that hybridized to the cDNA probe were purified, converted into "BLUESCRIPT" plasmids (Stratagene) according to the manufacturer's automatic excision protocol, and evaluated by restriction digests and gel electrophoresis. Sequence analysis revealed that one of the hybridizing cDNAs, designated "H2", encodes a portion of a putative G-protein coupled receptor (GPR), based on sequence comparisons to other GPRs.

A modified polymerase chain reaction (PCR) technique was used to clone the 5' cDNA for the H218 cDNA (Loh et al., 1989). H2 cDNA extends 2.6 kb to a 5' end that encodes part of the presumed extracellular N-terminal domain of the receptor. Thus, an oligodeoxynucleotide corresponding to the antisense strand of H2 (nucleotides 288 to 312 of H218) primed the first strand cDNA synthesis with MMLV Reverse Transcriptase (Gibco-BRL, Gaithersburg, Md.). Poly-A RNA extracted from postnatal day 14 (P14) rat lung served as a template. Terminal Deoxynucleotidyl Transferase (Gibco-BRL) was used to "tail" the resulting cDNA with guanines. The cDNA was then subjected to 35 rounds of PCR amplification with "AMPLITAQ" DNA polymerase (Perkin-Elmer, Branchburg, N.J.) The reaction was primed with an internal H2 specific primer containing antisense strand nucleotides 263 to 288 of H218 and a primer containing a poly-cytosine sequence. The resulting "18" cDNA was subcloned into a "BLUESCRIPT" plasmid (Stratagene) by exploiting restriction sites designed into the 5' ends of the PCR primers.

The "H2" and "18" cDNA fragments were then spliced together to form a 2.75 kb cDNA (designated "H218") containing a complete open reading frame (ORF) of 1052 bp that encodes a polypeptide of 352 amino acids.

Characterization of cDNA Clones

The nucleotide sequences of both strands of the H218 cDNA were determined by the dideoxy chain termination technique (Sanger et al., 1977). The T7 Sequencing kit (Pharmacia, Piscataway, N.J.) was used with denatured, double-stranded cDNAs in "BLUESCRIPT" plasmids serving as templates.

Tissue Preparation

For RNA preparations, Long Evans rats were killed by decapitation and their brains were immediately removed and dissected. Individual brain regions were frozen in liquid nitrogen. Rats and embryos of both sexes were used in the developmental study. Brains taken from embryos are designated with an "E" and those taken postnatally are designated with a "P" For example, a brain removed 20 days after birth would be P20.

RNA Preparation, Electrophoresis and Blotting

Frozen, dissected brain regions were pooled. The "FASTIRACK" kit (Invitrogen Corp., San Diego, Calif.) was used to extract Poly-A RNA from tissue culture cells and brain tissue used in the developmental study. Total RNA was extracted by homogenization in 4M guanidine thiocyanate followed by centrifugation through 5.7M CsCl according to the method of Chirgwin (Chirgwin et al., 1979). The RNA was purified by repeated ethanol precipitations, and its concentration was estimated spectrophotometrically from $A_{160}$. All RNA samples were stored at -20° C. as ethanol precipitates.

RNA (1–10μg of Poly-A or 20 μg of total) was denatured in 50% deionized formamide, 6.0% formaldehyde at 65° C. for 5 min and then size-fractionated by electrophoresis on a horizontal agarose gel (1.25%) containing 6.0% formaldehyde. The RNA was subsequently transferred to nylon membranes (ICN BIOTRANS membrane), which were then dried and baked at 80° C. for 2 hours under vacuum. Membranes were prehybridized for 2 hrs at 42° C. in 5X SSC, 50% formamide, 0.5% SDS, 50 mM sodium phosphate (pH 6.5) containing 250 μg/ml denatured salmon sperm DNA, 5X Denhardt's solution, and 100 μg/ml polyadenylic acid. The H2 cDNA probe was then $^{32}P$-labeled by random hexamer priming, and added to the prehybridization solution. After hybridization at 42° C. overnight, the membranes were washed twice for 30 min at room temperature in 2X SSC and twice for 45 min at 60° C. in 0.1X SSC, 0.1% SDS.

Membranes were exposed to X-ray film with two intensifying screens at -80° C. for several different time intervals in order to ensure that all comparisons were made within the linear sensitivity range of the film. The probe was then removed from the membranes by washing at 65° C. in 50% formamide, 10 mM sodium phosphate, pH 6.5%, for 1 hour. Stripped blots were rinsed in 2X SSC, 0.1% SDS and exposed to film to check for complete removal of probe. To correct for possible intersample variability in extraction, loading, or transfer of the RNA, the membranes were probed with $^{32}P$-labeled rat cDNA that recognizes ribosomal RNA or with a rat cyclophilin cDNA Brain cyclophilin mRNA levels are reported to be stable during brain development (Danielson et al., 1988).

Tissue Culture

Cells were grown on plates in Dulbecco's Modified Eagle Media (DMEM) containing 10% fetal bovine serum (FBS), with the exception of PC12 cells which were grown in RPMI media containing 10% horse serum and 5% FBS. Tissue culture cells were washed with 1X PBS, pH 7.4 while anchored to plates, mechanically dislodged, and collected by centrifugation for RNA extraction.

Antibody Production

Four peptides having amino acid sequences based on the deduced sequence of $p^{H218}$, and that correspond to separate extracellular and intracellular regions of $p^{H218}$ were synthesized by the Interdisciplinary Center for Biotechnology Research Core lab at the University of Florida. Rabbits were immunized with the peptides and antiserum prepared according to standard methods. Antisera (designated "1A") from the rabbit immunized with peptide 1 (SEQ ID NO.5) was purified by precipitation with 4.1M saturated ammonium sulfate at 25° C. overnight. The precipitate was dissolved in PBS and dialyzed against several changes of PBS. The 1A antibody was then affinity purified over a CNBr-Sepharose affinity column (Sigma Chemical, St. Louis, Mo.) to which the peptide 1 (SEQ ID NO.5) had been attached. Antibody was eluted with 0.1M glycine, pH 2.5.

Western Blotting

Crude cellular protein extract or membrane preparations from cell lines that express H218 mRNA were loaded onto a SDS-PAGE gel and electrophoresed. The proteins were then transferred to nitrocellulose paper and reacted with a 1:500 dilution of purified antibody. Rabbit antibody was then detected with a labeled second-step reagent specific for rabbit antibody.

Cloning of the rat-edg cDNA

A 1241 bp EcoRI-BamHI fragment of H2 cDNA was labeled with $^{32}p$ by random hexamer priming and used to screen approximately 7.5×10$^5$ cerebellar cDNAs of a rat cerebellar λ-ZAP library at medium stringency. The final hybridization wash was for 45 minutes at 47° C. in 2X SSC. Hybridizing clones were isolated for further evaluation. Purified clones were transferred into "BLUESCRIPT" plasmids (Stratagene) according to the manufacturer's protocol. Denatured double-stranded plasmids were sequenced by the dideoxy chain termination method (Sanger et al., 1977).

The following are examples which illustrate procedures and processes, including the best mode, for practicing the invention. These examples should not be construed as limiting, and are not intended to be a delineation of all possible modifications to the technique. All percentages are by weight and all solvent mixture proportions are by volume unless otherwise noted.

Example 1—Cloning and Sequence Analysis of H218

A rat hippocampal cDNA library was screened at medium stringency with a rat D2 dopamine receptor cDNA. One of the hybridizing cDNAs, designated "H2", encodes all but a few amino-terminal residues of a novel G-protein coupled receptor. A cDNA, designated "18", encoding the remaining amino-terminal residues was isolated using a modified PCR technique. The H218 cDNA was prepared from the two independent, overlapping cDNA clones "H2" and "18"which were isolated as described above. The H2 and 18 cDNAs were spliced together to yield a 2.75 kb cDNA containing a complete 1056 bp ORF encoding 352 amino acids. The corresponding gene will be referred to herein as H218, and the encoded GPR protein as pH218. The nucleotide sequence and the amino acid sequence that it encodes are shown in FIG. 1. The series of cytosines at the 5' end of the clone result from the PCR procedure used to isolate the "18" cDNA. A database search revealed that $p^{H218}$ is clearly a member of the GPR superfamily (FIG. 2).

Example 2—H218 mRNA Expression in Brain Tissue

Poly-A RNA was extracted from whole rat brain at multiple stages of development ranging from embryonic day 12 (E12) to postnatal day 80 (P80; adult). A Northern blot of the rat RNA was probed with the complete H2 cDNA. The blot was washed at progressively higher stringencies and exposed to X-ray film after each wash. The autoradiograph revealed an approximately 3.2 kb transcript at all stages of development (FIG. 3). However, H218 mRNA levels are much higher during brain embryogenesis than during later periods of brain development. This pattern indicates that H218 plays a role in cell proliferation and/or differentiation, which is prevalent during brain embryogenesis, rather than in neurotransmission, which is prevalent later in brain development. However, the H218 gene may be involved during all of these processes.

The autoradiographs following the high stringency wash also contain other bands and/or smears, primarily in the E15 and E18 lanes. These signals displayed a preferential reduction in intensity (relative to the 3.2 kb band) during the series of progressively higher stringency washes leading up to the high stringency wash. Therefore, they most likely represent DNA contamination and/or abundant cross hybridizing mRNAs that are related, but not identical, to H218 mRNA. It is also possible that they may partially represent additional ontogenetically regulated H218 transcripts. However, in a smaller scale Northern blot experiment which examined only E15, E18, and P14 brain H218 mRNA, a single 3.2 kb band at E15 and E18 was detected.

Example 3—H218 mRNA Expression in Other Tissue

Figures 4A, 4B:
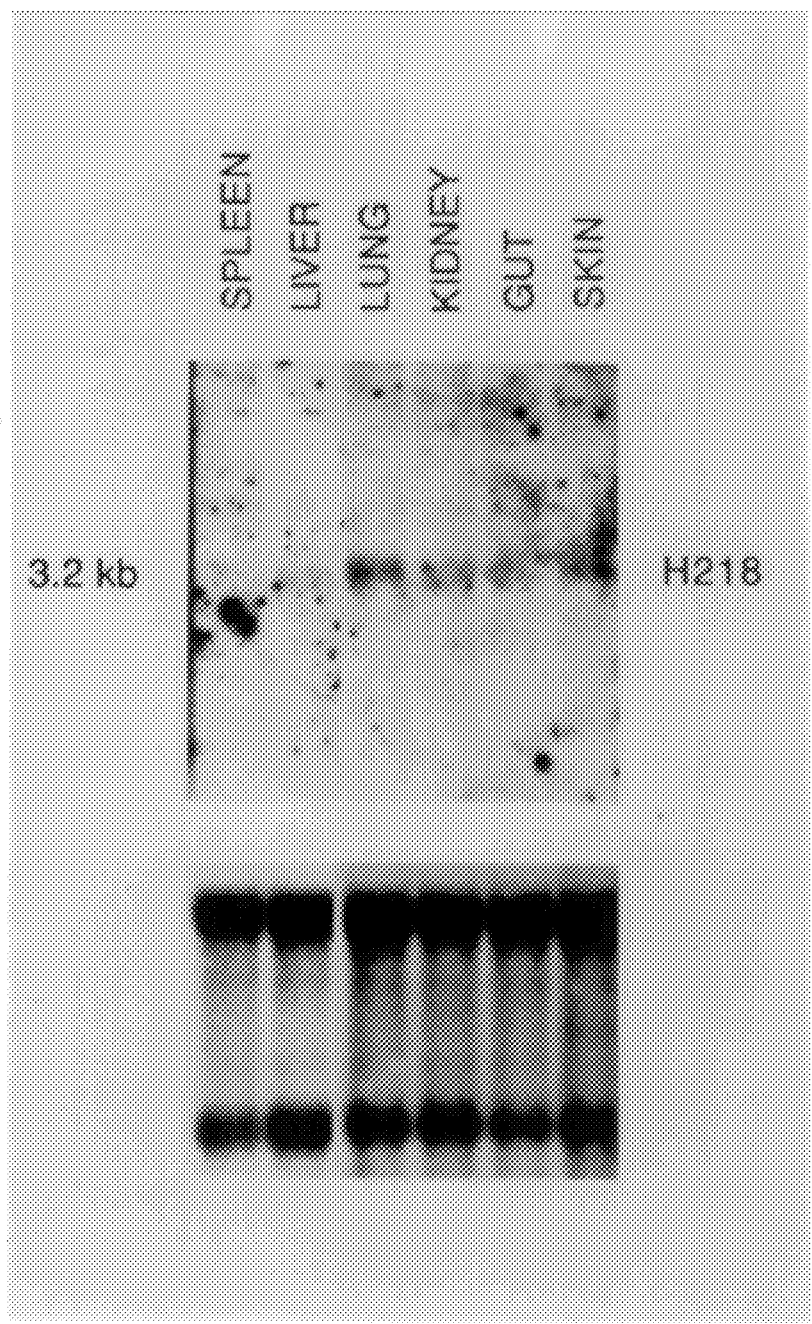
FIG. 4 shows an X-ray autoradiograph of a Northern blot illustrating the distribution of H218 mRNA in various tissues of the postnatal day 14 rat. Approximately 20 μg of total RNA was loaded per lane. The blot was probed for H218 mRNA (panel A), stripped, and then probed for rat ribosomal RNA (panel B) as an extraction, loading, and transfer control.

A Northern blot analysis of total RNA extracted from various organs of the postnatal day 14 (P14) rat was performed. The blot was probed with the H2 cDNA and washed at high stringency. A 3.2 kb H218 mRNA transcript was present in all tissues examined (FIG. 4). The H218 mRNA was most abundant in the lung. Less was found in the kidney, gut, and skin. A very low level of expression was detected in the spleen, brain and liver. This widespread distribution of H218 mRNA expression outside the brain at this stage of development is consistent with pH218 role in cell proliferation and/or differentiation.

Example 4—H218 mRNA Expression in Cell Lines

Northern blots were performed using poly-A RNA extracted from seven cell lines. The blots were probed with the H2 cDNA, washed at high stringency, and exposed to X-ray film. H218 mRNA was detected in all rodent cell lines examined. Thus, H218 mRNA is synthesized in B104 rat neuroblastoma cells, C6 rat glioma cells, PC12 rat pheochromocytoma cells, NB41A3 mouse neuroblastoma cells, D6P2T rat Schwannoma cells, NIH3T3 mouse fibroblasts, and RJK88 Chinese hamster fibroblasts. In all cases a prominent 3.2 kb band was observed after the high stringency wash, indicating that the sequence and size of the H218 mRNA transcript is highly conserved among mammals. The relative intensity of the band for each cell line is shown in Table 2.

TABLE 2

Relative H218 mRNA concentrations in cell lines

| | |
|---|---|
| B104 rat neuroblastoma cells | +++ |
| PC12 rat pheochromocytoma cells | ++ |
| C6 rat glioma cells | +++ |
| D6P2T rat Schwannoma cells | ++ |
| NB41A3 mouse neuroblastoma cells | + |
| NIH3T3 mouse fibroblasts | ++ |
| RJK88 hamster fibroblasts | ++ |

Of the cells lines and tissue samples examined, H218 mRNA is most abundant in the B104 neuroblastoma cells and the C6 glioma cells. The presence of relatively high concentrations of H218 mRNA in these primitive transformed cells further confirms that the H218 gene is expressed in the early stages of development.

Example 5—Manipulation of H218 mRNA levels using PMA and Nerve Growth Factor

RJK88 Chinese hamster fibroblasts were grown to approximately 80% confluence in Dulbecco's Modified Eagle Media (DMEM) containing 10% fetal bovine serum (FBS). The cells were then "serum-deprived" in DMEM containing 0.5% FBS for 2 days and subsequently treated with phorbol 12-myristate 13-acetate (PMA) at a final concentration of 200 ng/ml. Poly-A RNA was extracted 2 hrs after the initiation of PMA treatment. Control RJK88 cells (processed in parallel with PMA treated cells) were grown, serum-deprived, treated with the vehicle for PMA and extracted. A Northern blot performed using the RNA was probed with the H2 cDNA and washed under high stringency conditions. H218 mRNA was undetectable in the serum-deprived, "quiescent" control cells but was clearly present in the cells treated with PMA (FIG. 5).

The nerve growth factor (NGF)-induced differentiation of PC12 rat pheochromocytoma cells from a phenotype resembling proliferating, immature adrenal chromaffin cells to a phenotype resembling differentiated sympathetic neurons has been widely employed as a model of neuronal differentiation. A Northern blot was used to determine whether H218 expression in PC12 cells is affected by NGF stimulation. PC12 cells were grown in RPMI media supplemented with 5% FBS and 10% horse serum. The cells were then serum-deprived in RPMI media containing 0.3% FBS and 0.7% horse serum and treated with NGF (50 ng/ml, 2.5 S) 24 hours later. Poly-A RNA was extracted following 1, 4, or 8 hours of the NGF treatment. Control cells (processed in parallel) were treated identically except they received NGF vehicle instead of NGF. A Northern blot using the RNA was probed with the H2 cDNA and washed at high stringency.

NGF treatment rapidly decreases H218 mRNA concentrations in PC12 cells (FIG. 6). H218 mRNA levels (densitometrically quantitated and normalized to cyclophilin mRNA levels) decreased by 39%, 54%, and 33% following NGF treatment of 1, 4, and 8 hours respectively, but returned to normal by 24 hours of continuous NGF treatment. The apparently transient nature of the H218 mRNA decrease in PC12 cells is unlikely the result of any NGF lability given that 1) NGF is a stable compound in solution and 2) PC12 cells treated with NGF that is only replenished every 2 to 3 days (when the media is exchanged) undergo a continuous differentiation which is reversible upon withdrawal of NGF.

Example 6—Production and Characterization of Anti-$p^{H218}$ Antibodies

Rabbit antisera against four $p^{H218}$-derived synthetic peptides and having the amino acid sequences of SEQ ID NOS.5, 6, 7, and 8, respectively, were prepared. All antisera specifically recognize, with high titers, the appropriate immunogen peptide by ELISA assay. One of the antisera, designated 1A, has been affinity purified. The purified 1A antiserum recognizes two $p^{H218}$ bands on Western blots of cell lines that express H218 mRNA. Both bands were eliminated when the antiserum was preincubated with the antigen peptide but not when it was preincubated with an equal concentration of an irrelevant control peptide.

In addition, the bands were clearly much more intense from a stable cell line that has been engineered to overexpress $p^{H218}$. The lower (apparent molecular weight of about 50–55 kDa), and weaker, band resulted from monomeric $p^{H218}$ molecules since it roughly corresponds in size to the deduced amino acid sequence encoded by the H218 mRNA open reading frame. The upper (apparent molecular weight of about 180–200 kDa) and more intense band most likely results from an aggregated form of the protein.

The antibody titer in rabbits injected with $p^{H218}$ peptide 1 (SEQ ID NO.5) rises after the first few injections but drops thereafter, even with continued injections. This unexpected drop was not seen in the rabbits injected with other peptides. It is possible that the drop is the result of the anti-$p^{H218}$ antibodies in the rabbits blocking the function of $p^{H218}$ which, as discussed, may be involved in the cell proliferation events that are required for antibody production.

Example 7—Construction and Characterization of Stable Cell Lines with Increased or Decreased Levels of $p^{H218}$ PC12 cells were transfected with either 1) a vector designed to synthesize H218 mRNA and thereby lead to overexpression of $p^{H218,}$ 2) a vector designed to synthesize antisense H218 mRNA and thereby reduce expression of endogenous PC12 cell $p^{H218,}$ or 3) the empty vector (as a control). Several stable cell lines derived from each condition were isolated and characterized.

Northern blot analyses indicate that all isolated cell lines designed to overexpress H218 mRNA do express additional H218 mRNA derived from the transfected DNA. The transfected DNA was designed so that the resulting H218 mRNA would differ in size from mature PC12 cell H218 mRNA and therefore can be easily distinguished. Western blot analysis on one of the lines expressing the most H218 mRNA indicate that this line expressed significantly more $p^{H218}$ than vector transfected control lines.

Nerve growth factor (NGF) and basic fibroblast growth factor (bFGF) cause PC12 cells to differentiate from a phenotype resembling proliferating, immature cells to a phenotype resembling differentiated sympathetic neurons. This system has been extensively studied as a model of neuronal development. The effects of NGF and bFGF on our stable cell lines were examined to determine if manipulating $p^{H218}$ levels affects PC12 cell differentiation. The morphology of the cell lines was qualitatively recorded in two identical experiments by an observer unaware of the identity of the cell lines. The two cell lines overexpressing the most H218 mRNA, including the line shown to overexpress $p^{H218,}$ displayed a significantly less pronounced, growth factor induced change in cell body morphology when compared to vector transfected controls. Cell lines containing only a small amount of additional (exogenous DNA derived) H218 mRNA, including a line which does not detectably overexpress pH218 by Western blot analysis, displayed cell morphology changes indistinguishable from vector transfected controls.

Cell lines transfected with the "antisense" vector displayed a significantly more pronounced growth factor induced change in cell body morphology when compared with vector transfected controls. Therefore, increasing $p^{H218}$ levels decreases differentiation while decreasing the expression of $p^{H218}$ increases cell differentiation.

Example 8—Cloning of Human H218 Homolog

We have screened a human embryonic brain cDNA library using protocols as described for the cloning of the H218 cDNA and have isolated a cDNA which hybridizes under medium stringency conditions (two 45 minute washes at 42° C. in 2X SSC without formamide) to two non-overlapping fragments of the rat H218 cDNA. The pattern of restriction sites for this novel clone does not match the pattern of restriction sites found with the human edg cDNA clone, and is, therefore, a part of the human homolog of H218.

Example 9—Cloning and Sequence Analysis of rat-edg

A rat cerebellar cDNA library was screened using the H2 cDNA fragment of H218. The largest hybridizing cDNA was completely sequenced (FIG. 7). This 2234 bp cDNA, designated rat-edg, contains a 1149 bp ORF preceded by three in-frame stop codons. The cDNA contains an ATTTA motif in its 3' untranslated region. This motif has been associated with mRNA degradation. The cDNA will subsequently be referred to herein as rat-edg and the encoded protein as $p^{rat-edg}$.

Example 10—Expression of Rat-Edg in RNA in Tissue

The same Northern blot described in Example 2 was stripped and reprobed with the rat-edg cDNA. The blot was then washed at high stringency and exposed to X-ray film. Bands corresponding to an approximately 3.2 kb transcript were visible in all brain regions examined on the resulting autoradiograph. This size is close to the reported 3.0 kb size of human-edg. In contrast to H218 mRNA, the 3.2 kb rat-edg mRNA is preferentially expressed in later stages of postnatal development since a continual increase in mRNA expression is observed throughout development, with highest levels detected at P80. The 3.2 kb band observed following the high stringency wash was not the result of the rat-edg cDNA probe cross-hybridizing to H218 mRNA because: 1) the 3.2 kb transcript recognized by rat-edg displays a pattern of expression which is different from that of H218 mRNA, and 2) the in vitro transcribed H218 and rat-edg RNAs are specifically recognized on Northern blots by the appropriate probes.

A second set of generally weaker bands corresponding to a 4.9 kb transcript was also detected using the rat-edg cDNA. The 4.9 kb bands were not preferentially washed off during a series of progressively higher stringency washes and have been observed in multiple independent experiments. Therefore, they probably reflect an alternative rat-edg gene transcript. Interestingly, the expression of the 4.9 kb rat-edg RNA does not display an obvious trend during the developmental stages examined, and at E18, it is more abundant than the 3.2 kb transcript. In addition, the 4.9 kb rat-edg RNA was detected solely in brain RNA samples.

In addition, a Northern blot was performed with total RNA extracted from several regions of adult rat brain. The blot was probed with the rat-edg cDNA, washed at high stringency, and exposed to X-ray film. Rat-edg mRNA was comparably expressed in every region examined (i.e., the frontal cortex, striatum, ventral forebrain, hippocampus, cerebellum, and substantia nigra/ventral tegmental area). The 4.9 kb transcript may be preferentially expressed in the cerebellum, ventral forebrain, and frontal cortex.

The same Northern blot described in Example 3 was stripped and reprobed with the rat-edg cDNA The blot was washed at high stringency and exposed to X-ray film. At P14, rat-edg mRNA is expressed in the lung (approximately the same concentration as adult brain) and at a much lower concentration in the liver, spleen, and possibly kidney. However, in contrast to H218 mRNA, rat-edg mRNA was not detected in the gut or skin. As noted above, no 4.9 kb bands are detected in any of these regions although they were visible in lanes of the same Northern that were loaded with brain RNA.

Example 11—Expression of Rat-Edg RNA in Cell Lines

The Northern blots described in Example 4 were stripped and reprobed with rat-edg cDNA. They were subsequently washed at high stringency and exposed to X-ray film. Like H218 MRNA, rat-edg mRNA is expressed in NIH3T3 cells, C6 rat glioma cells, and rat PC12 pheochromocytoma cells. In contrast to H218 mRNA, rat-edg mRNA was not detected in RJK88 hamster fibroblasts, D6P2T rat Schwannoma cells, NB41A3 mouse neuroblastoma cells, or B104 neuroblastoma cells. Only the 3.2 kb transcript was detected in NIH3T3 and C6 cells, while only the 4.9 kb transcript is detected in PC12 cells.

It should be understood that the examples and embodiments described herein are for illustrative purposes only and that various modifications or changes in light thereof will be suggested to persons skilled in the art and are to be included within the scope and purview of this application and the scope of the appended claims.

REFERENCES

Yarden, Y., A. Ullrich (1988) Ann. Rev. Biochem. 57:443–478.
Devreotes, P. (1989) Science 245:1054–1058.
Hanley, M. R. (1989) Nature 340:97.
Zachary, I., P. J. Woll, E. Rozengurt (1987) Dev. Biol. 124:295–308.
Young, D., G. Waitches, C. Birchmeier, O. Fasano, M. Wigler (1986) Cell 45:711–719.
Gutkind, J. S., E. A. Novotny, M. R. Brann, K. C. Robbins (1991) Proc. Natl. Acad. Sci. USA 88:4703–4707.
Julius, D., T. J. Livelli, T. M. Jessell, R. Axel (1989) Science 244:1057–1062.
Julius, D., K. N. Huang, T. J. Livelli, R. Axel, T. M. Jessell (1990) Proc. Natl. Acad. Sci. USA 87:928–932.
MacLennan, A. J., G. D. Frantz, R. C. Weatherwax, N. J. K. Tillakaratne, A. J. Tobin (1990) Molec. Cell. Neurosci 1:151–160.
Loh, E. Y., J. F. Elliot, S. Cwirla, L. L. Lanier, M. M. Davis (1989) Science 243:217–220.
Sanger, F., S. Nicklen, A. R. Coulson (1977) Proc. Natl. Acad. Sci. USA 74:5463–5467.
Chirgwin, J. M., E. Przbyla, R. J. MacDonald, W. J. Rutter (1979) Biochem. 18:5294–5299.

I claim:

1. An isolated polynucleotide molecule which encodes a $p^{H218}$ polypeptide, said polynucleotide molecule comprising the nucleotide sequence shown in SEQ ID NO.1, or a polynucleotide molecule which hybridizes to said polynucleotide molecule under stringent hybridization conditions.

2. The polynucleotide molecule, according to claim 1, wherein said polynucleotide molecule comprises nucleotides 148 to 1203 of SEQ ID NO.1.

3. An isolated $p^{H218}$ polypeptide encoded by a polynucleotide molecule comprising the nucleotide sequence shown in SEQ ID NO:1, or a polynucleotide molecule which hybridizes to said polynucleotide molecule under stringent hybridization conditions.

4. The $p^{H218}$ polypeptide, according to claim 3, which is a protein of approximately 50 to 55 kDa molecular weight, as determined by Western blotting.

5. An isolated $p^{H218}$ peptide, wherein said peptide has an amino acid sequence shown in SEQ ID NO:5.

* * * * *

UNITED STATES PATENT AND TRADEMARK OFFICE
CERTIFICATE OF CORRECTION

PATENT NO. : 5,856,443
DATED : Jan. 5, 1999
INVENTOR(S) : Alexander John MacLennan It is certified that error appears in the above-identified patent and that said Letters Patent is hereby corrected as shown below:

Column 3, line 60: "cDNA" should read --cDNA.--.

Column 5, line 28: "mRNA This" should read --mRNA. This--.

Column 7, line 21: "$^{32}$p" should read --$^{32}$P--.

Column 8, line 31: "$A_{160}$" should read --$A_{260}$.--.

Column 9, line 30: "$^{32}$p" should read --$^{32}$P--.

Column 9, line 59: "pH218." should read --$p^{H218}$.--.

Column 12, line 16: "$p^{H218, 2)}$" should read --$p^{H218}$, 2)--.

Column 14, line 13: "H218 MRNA." should read --H218 mRNA--.

Column 14, line 44: "*Neurosci*" should read --*Neurosci.*--.

Signed and Sealed this

Twenty-first Day of March, 2000

Attest:

Attesting Officer

Q. TODD DICKINSON

*Commissioner of Patents and Trademarks*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 2754 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| CCCCCTCGAG | CACAGCCAAC | AGTCACCAAA | GTCAGCCACT | GGCTGTCCCG | GGGCGCAGAC | 60 |
| GCCAAGGCCA | CTCAGGCCAG | GGCAGGGACC | CTGGCCGGCC | TAGCCAGTGC | TCAGTCCCAT | 120 |
| GGCCCCGGCC | GGCCACTGAG | CCCCACCATG | GGCGGTTTAT | ACTCAGAGTA | CCTCAATCCT | 180 |
| GAGAAGGTTC | AGGAACACTA | CAATTACACC | AAGGAGACGC | TGGACATGCA | GGAGACGCCC | 240 |
| TCCCGCAAGG | TGGCCTCCGC | CTTCATCATC | ATTTTATGCT | GTGCCATCGT | GGTGGAGAAC | 300 |
| CTTCTGGTGC | TAATCGCAGT | GGCCAGGAAC | AGCAAGTTCC | ACTCAGCCAT | GTACCTGTTC | 360 |
| CTCGGCAACC | TGGCAGCCTC | CGACCTGCTG | GCAGGCGTGG | CCTTCGTGGC | CAACACCTTG | 420 |
| CTCTCCGGAC | CTGTCACCCT | GTCCTTAACT | CCCTTGCAGT | GGTTTGCCCG | AGAGGGTTCA | 480 |
| GCCTTCATCA | CGCTCTCTGC | CTCGGTCTTC | AGCCTCCTGG | CCATTGCCAT | CGAGAGACAA | 540 |
| GTGGCCATCG | CCAAGGTCAA | GCTCTACGGC | AGTGACAAAA | GCTGTCGAAT | GTTGATGCTC | 600 |
| ATTGGGGCCT | CTTGGCTGAT | ATCGCTGATT | CTGGGTGGCT | TGCCCATCCT | GGGCTGGAAT | 660 |
| TGTCTGGACC | ATCTGGAGGC | TTGCTCCACT | GTGCTGCCCC | TCTATGCTAA | GCACTATGTG | 720 |
| CTCTGCGTGG | TCACCATCTT | CTCTGTCATC | TTACTGGCTA | TCGTGGCCTT | GTACGTCCGA | 780 |
| ATCTACTTCG | TAGTCCGCTC | AAGCCATGCG | GACGTTGCTG | GTCCTCAGAC | GCTGGCCCTG | 840 |
| CTCAAGACAG | TCACCATCGT | ACTGGGTGTT | TTCATCATCT | GCTGGCTGCC | GGCTTTTAGC | 900 |
| ATCCTTCTCT | TAGACTCTAC | CTGTCCCGTC | CGGGCCTGTC | CTGTCCTCTA | CAAAGCCCAT | 960 |
| TATTTCTTTG | CCTTCGCCAC | CCTCAACTCT | CTGCTCAACC | CTGTCATCTA | TACATGGCGT | 1020 |
| AGCCGGGACC | TTCGGAGGGA | GGTACTGAGG | CCCCTGCTGT | GCTGGCGGCA | GGGGAAGGGA | 1080 |
| GCAACAGGGC | GCAGAGGTGG | GAACCCTGGT | CACCGACTCC | TGCCCCTCCG | CAGCTCCAGC | 1140 |
| TCCCTGGAGA | GAGGCTTGCA | TATGCCTACA | TCGCCAACAT | TTCTGGAGGG | CAACACAGTG | 1200 |
| GTCTGAGGGG | AAATGTGAAC | TGATCTGTAA | CCAAGCCACA | GAGAGAGCTC | TGTGGGGAGA | 1260 |
| GACCAGGTGA | CCTCATCATG | TCCCTCAGTG | CCACAGGTCT | GGAGGAACTG | ACCACGGCTC | 1320 |
| ATAGGTCAGG | TGGCCAACGG | AGGCACTGAC | TAATCAGATT | GTAGTACTGT | GACTGTGGGG | 1380 |
| ACCATTAAGG | GTCTAGGGGG | ACAGCAGGCT | CGAGTTTAGG | GCTAGACATT | TGCCACTTGG | 1440 |
| TACATAGGGT | GTCGGCATCC | TGTCTGTCCT | ATCTTCCAGC | TTCCCGGTTC | CCTTCCTGCC | 1500 |
| TCCTCCTTTT | AAGGGCCTCT | CTACATAGCC | CCGGCTGGCT | AGAGCTTGCT | GTGCAGACCA | 1560 |
| GGCTGACCTG | GACCTCCCAG | AGATAGATCA | ACTAACTGTG | TCCTGAGTGC | TGGGATTTTA | 1620 |
| AAGCCGTGTG | CCCCCACACC | CGGCTCCTGC | CACCTTCCAG | AAGCAATCTT | AGGCCACTTG | 1680 |
| TTGAGGAAAC | ACTCTCCCCA | GAGGACCCAA | GCCTTCTTCC | CTGTCTCTCT | GAGGCCTGAA | 1740 |
| TCCACAGCTT | CCCCATTTTA | TCAACTGCTG | CTTCTTCCCT | TTCCTTCTGT | GTTCAGGGGA | 1800 |
| AACCACTGTG | GGGGCAGGGA | GGGGTCCTGG | GATCCCAGTT | TTTATGCTCA | GATCTCACTG | 1860 |
| AGCACTTGCT | TTATTGGGGA | GCAGAGAGGA | ATCAGCTGAG | GCAGTGTGGG | GCAGATGTTG | 1920 |
| AGGAGAATTT | GGGCTTCCTG | GTGAGAAAAC | TCTAGGGGAG | GCGTTGGTTA | TTCCTGGAAC | 1980 |
| CCAGCCTCTC | TCCCCACGAA | CTCTTCACAC | CCGCAGCCTT | GAGCTGGATG | CAAAGGCTGC | 2040 |
| TTTCAATTTG | TCTTTGTAGT | TTTGTTTTGT | TTGTTTTGT | TTTTTAAAT | TGGGACAGGA | 2100 |
| TCTCACGTAC | CCCAGGCTGG | CCTCCGACTC | ACTATGTAGC | CAAGGCTGGC | TTTGGACTTC | 2160 |
| TGACCCTCCT | GCCTCCGCTT | CTGGAGTGCA | GGTATTACAA | GGGTGTACCA | CCACCACCAC | 2220 |
| CACCACCAAC | AACAACAACA | ACAACAACAC | CTGTCTTGAA | AACTATCATG | AATGACATGG | 2280 |

```
TTCACATAGC  CTTGGGTGGC  CAAGGACATC  CCGGATACTC  TTATGGCATC  TTCCTTGAAG    2340

GACTTTGCTA  AATCCTGTGG  AGAAGTAGAA  AATCCAATAC  GGTACAAACG  GTATTTATGT    2400

GTGTCTGTGT  ATCAGTGTGG  GGTCTGTGAC  CTCCTATCCC  AGTGTGGGTG  CTGTCTGACC    2460

TCTTATGTGC  ACATCCGTGT  CAAGACTGCT  AGAGAGATGG  ACGGGGTGT   GTGTGCTTGT    2520

GGGGGTCTAG  CCATGATCAG  GCCTCCTGGG  AATTGCTGAA  TCATCTCTCC  CACACACAGA    2580

CACACACCTC  CGCCTTAAAG  AAATGTGTGA  AAGAAAGGC   TGAGGAAGGG  GAGATTTGGG    2640

AGGCAAGGAG  CCAGTCGGGA  GTGTGTCTCC  CCTCATACAG  CTTCCCAGAT  GTCCCCCTTG    2700

TGCTGGAAAC  CCAGAACTGG  GCCAATAAAC  AGTTCAATTT  CTCTTGAAAA  AAAA          2754
```

( 2 ) INFORMATION FOR SEQ ID NO:2:

( i ) SEQUENCE CHARACTERISTICS:
        ( A ) LENGTH: 352 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met  Gly  Gly  Leu  Tyr  Ser  Glu  Tyr  Leu  Asn  Pro  Glu  Lys  Val  Gln  Glu
 1              5                        10                       15

His  Tyr  Asn  Tyr  Thr  Lys  Glu  Thr  Leu  Asp  Met  Gln  Glu  Thr  Pro  Ser
               20                       25                       30

Arg  Lys  Val  Ala  Ser  Ala  Phe  Ile  Ile  Ile  Leu  Cys  Cys  Ala  Ile  Val
               35                       40                       45

Val  Glu  Asn  Leu  Leu  Val  Leu  Ile  Ala  Val  Ala  Arg  Asn  Ser  Lys  Phe
          50                       55                       60

His  Ser  Ala  Met  Tyr  Leu  Phe  Leu  Gly  Asn  Leu  Ala  Ala  Ser  Asp  Leu
 65                       70                       75                       80

Leu  Ala  Gly  Val  Ala  Phe  Val  Ala  Asn  Thr  Leu  Leu  Ser  Gly  Pro  Val
                    85                       90                       95

Thr  Leu  Ser  Leu  Thr  Pro  Leu  Gln  Trp  Phe  Ala  Arg  Glu  Gly  Ser  Ala
               100                      105                      110

Phe  Ile  Thr  Leu  Ser  Ala  Ser  Val  Phe  Ser  Leu  Leu  Ala  Ile  Ala  Ile
               115                      120                      125

Glu  Arg  Gln  Val  Ala  Ile  Ala  Lys  Val  Lys  Leu  Tyr  Gly  Ser  Asp  Lys
          130                      135                      140

Ser  Cys  Arg  Met  Leu  Met  Leu  Ile  Gly  Ala  Ser  Trp  Leu  Ile  Ser  Leu
145                      150                      155                      160

Ile  Leu  Gly  Gly  Leu  Pro  Ile  Leu  Gly  Trp  Asn  Cys  Leu  Asp  His  Leu
                    165                      170                      175

Glu  Ala  Cys  Ser  Thr  Val  Leu  Pro  Leu  Tyr  Ala  Lys  His  Tyr  Val  Leu
               180                      185                      190

Cys  Val  Val  Thr  Ile  Phe  Ser  Val  Ile  Leu  Leu  Ala  Ile  Val  Ala  Leu
          195                      200                      205

Tyr  Val  Arg  Ile  Tyr  Phe  Val  Val  Arg  Ser  Ser  His  Ala  Asp  Val  Ala
          210                      215                      220

Gly  Pro  Gln  Thr  Leu  Ala  Leu  Leu  Lys  Thr  Val  Thr  Ile  Val  Leu  Gly
225                      230                      235                      240

Val  Phe  Ile  Ile  Cys  Trp  Leu  Pro  Ala  Phe  Ser  Ile  Leu  Leu  Leu  Asp
                    245                      250                      255

Ser  Thr  Cys  Pro  Val  Arg  Ala  Cys  Pro  Val  Leu  Tyr  Lys  Ala  His  Tyr
               260                      265                      270
```

```
              Phe  Phe  Ala  Phe  Ala  Thr  Leu  Asn  Ser  Leu  Leu  Asn  Pro  Val  Ile  Tyr
                        275                      280                      285

Thr  Trp  Arg  Ser  Arg  Asp  Leu  Arg  Arg  Glu  Val  Leu  Arg  Pro  Leu  Leu
                        290                      295                      300

Cys  Trp  Arg  Gln  Gly  Lys  Gly  Ala  Thr  Gly  Arg  Arg  Gly  Gly  Asn  Pro
              305                           310                      315                 320

Gly  His  Arg  Leu  Leu  Pro  Leu  Arg  Ser  Ser  Ser  Ser  Leu  Glu  Arg  Gly
                                  325                      330                      335

Leu  His  Met  Pro  Thr  Ser  Pro  Thr  Phe  Leu  Glu  Gly  Asn  Thr  Val  Val
                             340                      345                      350
```

( 2 ) INFORMATION FOR SEQ ID NO:3:

( i ) SEQUENCE CHARACTERISTICS:
        ( A ) LENGTH: 2232 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 269..1420

( x i ) SEQUENCE DESCRIPTION: SEQ ID NO:3:

```
GAATTCTTTG  CTGGTCTCCG  TCAGTCGCCG  ACAGCAGCAA  GATGCGGATC  GCGCGGTGTA         60

GACCCGGAGC  CCGGCGGACG  CAGCTTCGTC  CCGCTTGAGC  GAGGCTGCTG  TTTCTCGGAG        120

GCCTCTCCAG  CCAAGGAAAA  ACTACATAAA  AAAGCATCGG  ATTGCTTGCT  GACCTGGCCT        180

TGCTGTAACT  GAAGGCTCGC  TCAACCTCGC  CCTCTAGCGT  TTGTCTGGAG  AAGTACCACC        240

CCGGGCTCCT  GGGGACACAG  TTGCGGCT  ATG  GTG  TCC  TCC  ACC  AGC  ATC  CCA      292
                                  Met  Val  Ser  Ser  Thr  Ser  Ile  Pro
                                   1                 5

GTG  GTT  AAG  GCT  CTC  CGC  AGC  CAA  GTC  TCC  GAC  TAT  GGC  AAC  TAT  GAT    340
Val  Val  Lys  Ala  Leu  Arg  Ser  Gln  Val  Ser  Asp  Tyr  Gly  Asn  Tyr  Asp
     10                  15                      20

ATC  ATA  GTC  CGG  CAT  TAC  AAC  TAC  ACA  GGC  AAG  CTG  AAC  ATC  GGA  GTG    388
Ile  Ile  Val  Arg  His  Tyr  Asn  Tyr  Thr  Gly  Lys  Leu  Asn  Ile  Gly  Val
25                       30                      35                       40

GAG  AAG  GAC  CAT  GGC  ATT  AAA  CTG  ACT  TCA  GTG  GTG  TTC  ATT  CTC  ATC    436
Glu  Lys  Asp  His  Gly  Ile  Lys  Leu  Thr  Ser  Val  Val  Phe  Ile  Leu  Ile
                      45                      50                      55

TGC  TGC  TTG  ATC  ATC  CTA  GAG  AAT  ATA  TTT  GTC  TTG  CTA  ACT  ATT  TGG    484
Cys  Cys  Leu  Ile  Ile  Leu  Glu  Asn  Ile  Phe  Val  Leu  Leu  Thr  Ile  Trp
                60                      65                      70

AAA  ACC  AAG  AAG  TTC  CAC  CGG  CCC  ATG  TAC  TAT  TTC  ATA  GGC  AAC  CTA    532
Lys  Thr  Lys  Lys  Phe  His  Arg  Pro  Met  Tyr  Tyr  Phe  Ile  Gly  Asn  Leu
     75                      80                      85

GCC  CTC  TCG  GAC  CTG  TTA  GCA  GGA  GTG  GCT  TAC  ACA  GCT  AAC  CTG  CTG    580
Ala  Leu  Ser  Asp  Leu  Leu  Ala  Gly  Val  Ala  Tyr  Thr  Ala  Asn  Leu  Leu
     90                      95                     100

TTG  TCT  GGG  GCC  ACC  ACC  TAC  AAG  CTC  ACA  CCT  GCC  CAG  TGG  TTT  CTG    628
Leu  Ser  Gly  Ala  Thr  Thr  Tyr  Lys  Leu  Thr  Pro  Ala  Gln  Trp  Phe  Leu
105                      110                     115                     120

CGG  GAA  GGA  AGT  ATG  TTT  GTG  GCT  CTG  TCT  GCC  TCA  GTC  TTC  AGC  CTC    676
Arg  Glu  Gly  Ser  Met  Phe  Val  Ala  Leu  Ser  Ala  Ser  Val  Phe  Ser  Leu
                     125                     130                     135

CTT  GCT  ATC  GCC  ATT  GAG  CGC  TAC  ATC  ACC  ATG  CTG  AAG  ATG  AAA  CTA    724
Leu  Ala  Ile  Ala  Ile  Glu  Arg  Tyr  Ile  Thr  Met  Leu  Lys  Met  Lys  Leu
                140                     145                     150
```

```
CAC  AAC  GGC  AGC  AAC  AGC  TCG  CGC  TCC  TTT  CTG  CTG  ATC  AGT  GCC  TGC     772
His  Asn  Gly  Ser  Asn  Ser  Ser  Arg  Ser  Phe  Leu  Leu  Ile  Ser  Ala  Cys
          155                      160                      165

TGG  GTC  ATC  TCC  CTC  ATC  CTG  GGT  GGG  CTG  CCC  ATC  ATG  GGC  TGG  AAC     820
Trp  Val  Ile  Ser  Leu  Ile  Leu  Gly  Gly  Leu  Pro  Ile  Met  Gly  Trp  Asn
     170                      175                      180

TGC  ATC  AGC  TCG  CTG  TCC  AGC  TGC  TCC  ACC  GTG  CTC  CCG  CTC  TAC  CAC     868
Cys  Ile  Ser  Ser  Leu  Ser  Ser  Cys  Ser  Thr  Val  Leu  Pro  Leu  Tyr  His
185                      190                      195                      200

AAG  CAC  TAT  ATT  CTC  TTC  TGC  ACC  ACC  GTC  TTC  ACC  CTG  CTC  CTG  CTT     916
Lys  His  Tyr  Ile  Leu  Phe  Cys  Thr  Thr  Val  Phe  Thr  Leu  Leu  Leu  Leu
                    205                      210                      215

TCC  ATC  GTC  ATC  CTC  TAC  TGC  AGG  ATC  TAC  TCC  TTG  GTG  AGG  ACT  CGA     964
Ser  Ile  Val  Ile  Leu  Tyr  Cys  Arg  Ile  Tyr  Ser  Leu  Val  Arg  Thr  Arg
               220                      225                      230

AGC  CGC  CGC  CTG  ACC  TTC  CGC  AAG  AAC  ATC  TCC  AAG  GCC  AGC  CGC  AGT    1012
Ser  Arg  Arg  Leu  Thr  Phe  Arg  Lys  Asn  Ile  Ser  Lys  Ala  Ser  Arg  Ser
          235                      240                      245

TCC  GAG  AAG  TCT  CTG  GCC  TTG  CTG  AAG  ACA  GTG  ATC  ATT  GTC  CTG  AGT    1060
Ser  Glu  Lys  Ser  Leu  Ala  Leu  Leu  Lys  Thr  Val  Ile  Ile  Val  Leu  Ser
250                      255                      260

GTC  TTC  ATT  GCC  TGC  TGG  GCC  CCT  CTC  TTC  ATC  CTA  CTA  CTT  TTA  GAT    1108
Val  Phe  Ile  Ala  Cys  Trp  Ala  Pro  Leu  Phe  Ile  Leu  Leu  Leu  Leu  Asp
265                      270                      275                      280

GTG  GGG  TGC  AAG  GCG  AAG  ACC  TGT  GAC  ATC  CTG  TAC  AAA  GCA  GAG  TAC    1156
Val  Gly  Cys  Lys  Ala  Lys  Thr  Cys  Asp  Ile  Leu  Tyr  Lys  Ala  Glu  Tyr
                    285                      290                      295

TTC  CTG  GTT  CTG  GCT  GTG  CTG  AAC  TCA  GGT  ACC  AAC  CCC  ATC  ATC  TAC    1204
Phe  Leu  Val  Leu  Ala  Val  Leu  Asn  Ser  Gly  Thr  Asn  Pro  Ile  Ile  Tyr
               300                      305                      310

ACT  CTG  ACC  AAT  AAG  GAG  ATG  CGC  CGG  GCC  TTC  ATC  AGG  ATC  ATA  TCT    1252
Thr  Leu  Thr  Asn  Lys  Glu  Met  Arg  Arg  Ala  Phe  Ile  Arg  Ile  Ile  Ser
          315                      320                      325

TGT  TGC  AAA  TGC  CCC  AAC  GGA  GAC  TCC  GCT  GGC  AAA  TTC  AAG  AGG  CCC    1300
Cys  Cys  Lys  Cys  Pro  Asn  Gly  Asp  Ser  Ala  Gly  Lys  Phe  Lys  Arg  Pro
330                      335                      340

ATC  ATC  CCG  GGC  ATG  GAA  TTT  AGC  CGC  AGC  AAA  TCA  GAC  AAC  TCC  TCC    1348
Ile  Ile  Pro  Gly  Met  Glu  Phe  Ser  Arg  Ser  Lys  Ser  Asp  Asn  Ser  Ser
345                      350                      355                      360

CAC  CCC  CAG  AAG  GAT  GAT  GGG  GAC  AAT  CCA  GAG  ACC  ATT  ATG  TCT  TCT    1396
His  Pro  Gln  Lys  Asp  Asp  Gly  Asp  Asn  Pro  Glu  Thr  Ile  Met  Ser  Ser
                    365                      370                      375

GGA  AAC  GTC  AAT  TCT  TCT  TCT  TAAAACCGGA  AGCTGTTGAT  ACTGTTGATT              1447
Gly  Asn  Val  Asn  Ser  Ser  Ser
               380

CTGGCTTCAT  CACTCACTAC  CCTAGCATTT  CAAAAACATC  TCTCTTTCTC  CACTGCTGCA           1507

AGGAAGAAGC  AGCCGGGAGC  CTGAGAGAGG  GAGGGAAGGG  AGAATGTGCG  GCTTGGTGAT           1567

ACCATGTTGT  AGGTAGGTTA  TGATTATGAA  CAATGCCCTG  GGAAGGGTGG  AGATCAGATC           1627

TGCCTGCAGA  GGGTTTCCTG  CCCCCTCCTA  ATCTCTTCAC  TTCCTTCAGT  CGTTTCTGTT           1687

TATCCCCCAT  ACTCTTTTTT  CTTTTCTCCG  TTTTTCTCAT  TCCCCTTCTC  TACCATCGCT           1747

TTCTTTTCTC  TTTCTTTAAA  ATTTAGGGGC  AACAAAGGA   ATCCACAAA   TGGATATTGT           1807

GGAAAACATA  GTGCTGAATG  ACGGCAAAGA  ATGGTGGTAA  ATCAAAGAT   AAATTAACTT           1867

CATAAGACTG  CTATTCTGAA  ATGCAACAAT  CTTGTACAGT  CAGGACTGAT  AAAATGGAGC           1927

AATCAGACAT  TTCAGATGCC  CGTCAATGTA  AAATCACCTA  CTTGAACATT  GTATGCAATA           1987

CATTCACACA  AAAAAGCAAA  TACTGTAGCC  TTATTTGAAC  AATACTGAAC  TCATAAATAC           2047
```

```
TCATGGTTTC ACTCTGTCCA GGCGCCTAAG GACTATGCTG CTGTAATACA GGAAAACACA      2107

GCGGATGCCT CCTCTATTAA AATGTCACTC AAGAAAAGTC TCTTGTAACG TAAAGGCAAA      2167

CACATGTAGC TACTGAGCTA TGACTGTCCT TGGTCACACT CTATGGGAAA AACACCGGAC      2227

TCCAC                                                                  2232
```

( 2 ) INFORMATION FOR SEQ ID NO:4:

( i ) SEQUENCE CHARACTERISTICS:
        ( A ) LENGTH: 383 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Val Ser Ser Thr Ser Ile Pro Val Val Lys Ala Leu Arg Ser Gln
 1               5                  10                  15

Val Ser Asp Tyr Gly Asn Tyr Asp Ile Val Arg His Tyr Asn Tyr
            20                  25                  30

Thr Gly Lys Leu Asn Ile Gly Val Glu Lys Asp His Gly Ile Lys Leu
            35                  40                  45

Thr Ser Val Val Phe Ile Leu Ile Cys Cys Leu Ile Ile Leu Glu Asn
    50                  55                  60

Ile Phe Val Leu Leu Thr Ile Trp Lys Thr Lys Lys Phe His Arg Pro
65                  70                  75                  80

Met Tyr Tyr Phe Ile Gly Asn Leu Ala Leu Ser Asp Leu Leu Ala Gly
                85                  90                  95

Val Ala Tyr Thr Ala Asn Leu Leu Leu Ser Gly Ala Thr Thr Tyr Lys
                100                 105                 110

Leu Thr Pro Ala Gln Trp Phe Leu Arg Glu Gly Ser Met Phe Val Ala
            115                 120                 125

Leu Ser Ala Ser Val Phe Ser Leu Leu Ala Ile Ala Ile Glu Arg Tyr
    130                 135                 140

Ile Thr Met Leu Lys Met Lys Leu His Asn Gly Ser Asn Ser Ser Arg
145                 150                 155                 160

Ser Phe Leu Leu Ile Ser Ala Cys Trp Val Ile Ser Leu Ile Leu Gly
                165                 170                 175

Gly Leu Pro Ile Met Gly Trp Asn Cys Ile Ser Ser Leu Ser Ser Cys
                180                 185                 190

Ser Thr Val Leu Pro Leu Tyr His Lys His Tyr Ile Leu Phe Cys Thr
            195                 200                 205

Thr Val Phe Thr Leu Leu Leu Leu Ser Ile Val Ile Leu Tyr Cys Arg
    210                 215                 220

Ile Tyr Ser Leu Val Arg Thr Arg Ser Arg Arg Leu Thr Phe Arg Lys
225                 230                 235                 240

Asn Ile Ser Lys Ala Ser Arg Ser Ser Glu Lys Ser Leu Ala Leu Leu
                245                 250                 255

Lys Thr Val Ile Ile Val Leu Ser Val Phe Ile Ala Cys Trp Ala Pro
            260                 265                 270

Leu Phe Ile Leu Leu Leu Leu Asp Val Gly Cys Lys Ala Lys Thr Cys
    275                 280                 285

Asp Ile Leu Tyr Lys Ala Glu Tyr Phe Leu Val Leu Ala Val Leu Asn
    290                 295                 300

Ser Gly Thr Asn Pro Ile Ile Tyr Thr Leu Thr Asn Lys Glu Met Arg
305                 310                 315                 320
```

Arg Ala Phe Ile Arg Ile Ile Ser Cys Cys Lys Cys Pro Asn Gly Asp
                325                     330                     335

Ser Ala Gly Lys Phe Lys Arg Pro Ile Ile Pro Gly Met Glu Phe Ser
            340                     345                 350

Arg Ser Lys Ser Asp Asn Ser Ser His Pro Gln Lys Asp Asp Gly Asp
        355                     360                 365

Asn Pro Glu Thr Ile Met Ser Ser Gly Asn Val Asn Ser Ser Ser
    370                     375                 380

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Lys Glu Thr Leu Asp Met Gln Glu Thr Pro Ser Arg
 1                5                   10

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Tyr Ser Glu Tyr Leu Asn Pro Glu Lys Val Gln Glu
 1                5                   10

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Arg Gln Gly Lys Gly Ala Thr Gly Arg Arg Gly Gly
 1                5                   10

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Arg Ser Ser Ser Ser Leu Glu Arg Gly Leu His Met
 1                5                   10

( 2 ) INFORMATION FOR SEQ ID NO:9:

( i ) SEQUENCE CHARACTERISTICS:
        ( A ) LENGTH: 303 amino acids
        ( B ) TYPE: amino acid
        ( C ) STRANDEDNESS: Not Relevant -continued (D) TOPOLOGY: Not Relevant (ii) MOLECULE TYPE: protein (xi) SEQUENCE DESCRIPTION: SEQ ID NO:9:

| Met | Asp | Pro | Leu | Asn | Leu | Ser | Trp | Tyr | Asp | Asp | Leu | Glu | Arg | Gln |
|---|---|---|---|---|---|---|---|---|---|---|---|---|---|---|
| 1 | | | | 5 | | | | | 10 | | | | | 15 |
| Asn | Trp | Ser | Arg | Pro | Phe | Asn | Gly | Ser | Glu | Gly | Lys | Ala | Asp | Arg | Pro |
| | | | 20 | | | | | 25 | | | | | 30 | |
| His | Tyr | Asn | Tyr | Tyr | Ala | Met | Leu | Leu | Thr | Leu | Leu | Ile | Phe | Ile | Ile |
| | | 35 | | | | | 40 | | | | | 45 | | | |
| Val | Phe | Gly | Asn | Val | Leu | Val | Cys | Met | Ala | Val | Ser | Arg | Glu | Lys | Ala |
| | | 50 | | | | 55 | | | | | 60 | | | | |
| Leu | Gln | Thr | Thr | Thr | Asn | Tyr | Leu | Ile | Val | Ser | Leu | Ala | Val | Ala | Asp |
| 65 | | | | | 70 | | | | | 75 | | | | | 80 |
| Leu | Leu | Val | Ala | Thr | Leu | Val | Met | Pro | Trp | Val | Val | Tyr | Leu | Glu | Val |
| | | | | 85 | | | | | 90 | | | | | 95 | |
| Val | Gly | Glu | Trp | Lys | Phe | Ser | Arg | Ile | His | Cys | Asp | Ile | Phe | Val | Thr |
| | | | 100 | | | | | 105 | | | | | 110 | | |
| Leu | Asp | Val | Met | Met | Cys | Thr | Ala | Ser | Ile | Leu | Asn | Leu | Cys | Ala | Ile |
| | | | 115 | | | | 120 | | | | | 125 | | | |
| Ser | Ile | Asp | Arg | Tyr | Thr | Ala | Val | Ala | Met | Pro | Met | Leu | Tyr | Asn | Thr |
| | | 130 | | | | | 135 | | | | | 140 | | | |
| Arg | Tyr | Ser | Ser | Lys | Arg | Arg | Val | Thr | Val | Met | Ile | Ala | Ile | Val | Trp |
| 145 | | | | | 150 | | | | | 155 | | | | | 160 |
| Val | Leu | Ser | Phe | Thr | Ile | Ser | Cys | Pro | Leu | Leu | Phe | Gly | Leu | Asn | Asn |
| | | | | 165 | | | | | 170 | | | | | 175 | |
| Thr | Asp | Gln | Asn | Glu | Cys | Ile | Ile | Ala | Asn | Pro | Ala | Phe | Val | Val | Tyr |
| | | | 180 | | | | | 185 | | | | | 190 | | |
| Ser | Ser | Ile | Val | Ser | Phe | Tyr | Val | Pro | Phe | Ile | Val | Thr | Leu | Leu | Val |
| | | 195 | | | | | 200 | | | | | 205 | | | |
| Tyr | Ile | Lys | Ile | Tyr | Ile | Val | Leu | Arg | Lys | Arg | Arg | Lys | Arg | Val | Asn |
| | | 210 | | | | | 215 | | | | | 220 | | | |
| Thr | Lys | Lys | Glu | Lys | Lys | Ala | Thr | Gln | Met | Leu | Ala | Ile | Val | Leu | Gly |
| 225 | | | | | 230 | | | | | 235 | | | | | 240 |
| Val | Phe | Ile | Ile | Cys | Trp | Leu | Pro | Phe | Phe | Ile | Thr | His | Ile | Leu | Asn |
| | | | | 245 | | | | | 250 | | | | | 255 | |
| Ile | His | Cys | Asp | Cys | Asn | Ile | Pro | Pro | Val | Leu | Tyr | Ser | Ala | Phe | Thr |
| | | | 260 | | | | | 265 | | | | | 270 | | |
| Trp | Leu | Gly | Tyr | Val | Asn | Ser | Ala | Val | Asn | Pro | Ile | Ile | Tyr | Thr | Thr |
| | | 275 | | | | | 280 | | | | | 285 | | | |
| Phe | Asn | Ile | Glu | Phe | Arg | Lys | Ala | Phe | Met | Lys | Ile | Leu | His | Cys | |
| | 290 | | | | | 295 | | | | | 300 | | | | |

(2) INFORMATION FOR SEQ ID NO:10:

(i) SEQUENCE CHARACTERISTICS:
(A) LENGTH: 377 amino acids
(B) TYPE: amino acid
(C) STRANDEDNESS: Not Relevant
(D) TOPOLOGY: Not Relevant (ii) MOLECULE TYPE: protein (xi) SEQUENCE DESCRIPTION: SEQ ID NO:10:

| Met | Gly | Pro | Pro | Gly | Asn | Asp | Ser | Asp | Phe | Leu | Leu | Thr | Thr | Asn | Gly |
|---|---|---|---|---|---|---|---|---|---|---|---|---|---|---|---|
| 1 | | | | 5 | | | | | 10 | | | | | 15 | |
| Ser | His | Val | Pro | Asp | His | Asp | Val | Thr | Glu | Glu | Arg | Asp | Glu | Ala | Trp |

|   |   |   |   |   | 20 |   |   |   |   | 25 |   |   |   |   | 30 |
|---|---|---|---|---|----|---|---|---|---|----|---|---|---|---|----|

| Val | Val | Gly | Met | Ala | Ile | Leu | Met | Ser | Val | Ile | Val | Leu | Ala | Ile | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |
| Phe | Gly | Asn | Val | Leu | Val | Ile | Thr | Ala | Ile | Ala | Lys | Phe | Glu | Arg | Leu |
|     |     | 50  |     |     |     | 55  |     |     |     |     |     | 60  |     |     |     |
| Gln | Thr | Val | Thr | Asn | Tyr | Phe | Ile | Thr | Ser | Leu | Ala | Cys | Ala | Asp | Leu |
| 65  |     |     |     |     | 70  |     |     |     |     | 75  |     |     |     |     | 80  |
| Val | Met | Gly | Leu | Ala | Val | Val | Pro | Phe | Gly | Ala | Ser | His | Ile | Leu | Met |
|     |     |     |     | 85  |     |     |     |     | 90  |     |     |     |     | 95  |     |
| Lys | Met | Trp | Asn | Phe | Gly | Asn | Phe | Trp | Cys | Glu | Phe | Trp | Thr | Ser | Ile |
|     |     |     | 100 |     |     |     |     | 105 |     |     |     | 110 |     |     |     |
| Asp | Val | Leu | Cys | Val | Thr | Ala | Ser | Ile | Glu | Thr | Leu | Cys | Val | Ile | Ala |
|     |     | 115 |     |     |     |     | 120 |     |     |     |     | 125 |     |     |     |
| Val | Asp | Arg | Tyr | Ile | Ala | Ile | Thr | Ser | Pro | Phe | Lys | Tyr | Gln | Ser | Leu |
|     | 130 |     |     |     |     | 135 |     |     |     |     | 140 |     |     |     |     |
| Leu | Thr | Lys | Asn | Lys | Ala | Arg | Met | Val | Ile | Leu | Met | Val | Trp | Ile | Val |
| 145 |     |     |     |     | 150 |     |     |     |     | 155 |     |     |     |     | 160 |
| Ser | Gly | Leu | Thr | Ser | Phe | Leu | Pro | Ile | Gln | Met | His | Trp | Tyr | Arg | Ala |
|     |     |     |     | 165 |     |     |     |     | 170 |     |     |     |     | 175 |     |
| Thr | His | Gln | Lys | Ala | Ile | Asp | Cys | Tyr | His | Arg | Glu | Thr | Cys | Cys | Asp |
|     |     |     | 180 |     |     |     |     | 185 |     |     |     |     | 190 |     |     |
| Phe | Phe | Thr | Asn | Gln | Ala | Tyr | Ala | Ile | Ala | Ser | Ser | Ile | Val | Ser | Phe |
|     |     | 195 |     |     |     |     | 200 |     |     |     |     | 205 |     |     |     |
| Tyr | Val | Pro | Leu | Val | Val | Met | Val | Phe | Val | Tyr | Ser | Arg | Val | Phe | Gln |
|     | 210 |     |     |     |     | 215 |     |     |     |     | 220 |     |     |     |     |
| Val | Ala | Lys | Arg | Gln | Leu | Gln | Lys | Xaa | Xaa | Xaa | Xaa | Xaa | Xaa | Xaa | Xaa |
| 225 |     |     |     |     | 230 |     |     |     |     | 235 |     |     |     |     | 240 |
| Xaa | Xaa | Xaa | Xaa | Xaa | Xaa | Xaa | Xaa | Xaa | Xaa | Xaa | Xaa | Xaa | Xaa | Xaa | Xaa |
|     |     |     |     | 245 |     |     |     |     | 250 |     |     |     |     | 255 |     |
| Xaa | Xaa | Xaa | Xaa | Xaa | Xaa | Xaa | Xaa | Lys | Glu | His | Lys | Ala | Leu | Lys |     |
|     |     |     |     | 260 |     |     |     |     | 265 |     |     |     |     | 270 |     |
| Thr | Leu | Gly | Ile | Ile | Met | Gly | Ile | Phe | Thr | Leu | Cys | Trp | Leu | Pro | Phe |
|     |     | 275 |     |     |     |     | 280 |     |     |     |     | 285 |     |     |     |
| Phe | Ile | Val | Asn | Ile | Val | His | Val | Ile | Gln | Asp | Asn | Leu | Ile | Pro | Lys |
|     | 290 |     |     |     |     | 295 |     |     |     |     | 300 |     |     |     |     |
| Glu | Val | Tyr | Ile | Leu | Leu | Asn | Trp | Leu | Gly | Tyr | Val | Asn | Ser | Ala | Phe |
| 305 |     |     |     |     | 310 |     |     |     |     | 315 |     |     |     |     | 320 |
| Asn | Pro | Leu | Ile | Tyr | Cys | Arg | Ser | Pro | Asp | Phe | Arg | Ile | Ala | Phe | Gln |
|     |     |     |     | 325 |     |     |     |     | 330 |     |     |     |     | 335 |     |
| Glu | Leu | Leu | Cys | Xaa | Xaa | Xaa | Xaa | Xaa | Xaa | Xaa | Xaa | Xaa | Xaa | Xaa | Xaa |
|     |     |     | 340 |     |     |     |     | 345 |     |     |     |     | 350 |     |     |
| Xaa | Xaa | Xaa | Xaa | Xaa | Xaa | Xaa | Xaa | Xaa | Xaa | Xaa | Xaa | Xaa | Xaa | Xaa | Xaa |
|     |     | 355 |     |     |     |     | 360 |     |     |     |     | 365 |     |     |     |
| Xaa | Xaa | Xaa | Xaa | Xaa | Xaa | Xaa | Xaa | Xaa |     |     |     |     |     |     |     |
|     | 370 |     |     |     |     | 375 |     |     |     |     |     |     |     |     |     |

( 2 ) INFORMATION FOR SEQ ID NO:11:

( i ) SEQUENCE CHARACTERISTICS:
        ( A ) LENGTH: 450 amino acids
        ( B ) TYPE: amino acid
        ( C ) STRANDEDNESS: Not Relevant
        ( D ) TOPOLOGY: Not Relevant ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Met 1 | Gly | Ser | Leu | Gln 5 | Pro | Asp | Ala | Gly | Asn 10 | Ala | Ser | Trp | Asn | Gly 15 | Thr |
| Glu | Ala | Pro | Gly 20 | Gly | Gly | Ala | Arg | Ala 25 | Thr | Pro | Tyr | Ser | Leu 30 | Gln | Val |
| Thr | Leu | Thr 35 | Leu | Val | Cys | Leu | Ala 40 | Gly | Leu | Leu | Met | Leu 45 | Leu | Thr | Val |
| Phe | Gly 50 | Asn | Val | Leu | Val | Ile 55 | Ile | Ala | Val | Phe | Thr 60 | Ser | Arg | Ala | Leu |
| Lys 65 | Ala | Pro | Gln | Asn | Leu 70 | Phe | Leu | Val | Ser | Leu 75 | Ala | Ser | Ala | Asp | Ile 80 |
| Leu | Val | Ala | Thr | Leu 85 | Val | Ile | Pro | Phe | Ser 90 | Leu | Ala | Asn | Glu | Val 95 | Met |
| Gly | Tyr | Trp | Tyr 100 | Phe | Gly | Lys | Thr | Trp 105 | Cys | Glu | Ile | Tyr | Leu 110 | Ala | Leu |
| Asp | Val | Leu 115 | Phe | Cys | Thr | Ser | Ser 120 | Ile | Val | His | Leu | Cys 125 | Ala | Ile | Ser |
| Leu | Asp 130 | Arg | Tyr | Trp | Ser | Ile 135 | Thr | Gln | Ala | Ile | Glu 140 | Tyr | Asn | Leu | Lys |
| Arg 145 | Thr | Pro | Arg | Arg | Ile 150 | Lys | Ala | Ile | Ile | Ile 155 | Thr | Val | Trp | Val | Ile 160 |
| Ser | Ala | Val | Ile | Ser 165 | Phe | Pro | Pro | Leu | Ile 170 | Ser | Ile | Glu | Lys | Lys 175 | Gly |
| Gly | Gly | Gly | Gly 180 | Pro | Gln | Pro | Ala | Glu 185 | Pro | Arg | Cys | Glu | Ile 190 | Asn | Asp |
| Gln | Lys | Trp | Tyr 195 | Val | Ile | Ser | Ser | Cys 200 | Ile | Gly | Ser | Phe | Phe 205 | Ala | Pro |
| Cys | Leu 210 | Ile | Met | Ile | Leu | Val 215 | Tyr | Val | Arg | Ile | Tyr 220 | Gln | Ile | Ala | Lys |
| Arg 225 | Arg | Thr | Arg | Val | Xaa 230 | Xaa | Xaa | Xaa | Xaa | Xaa 235 | Xaa | Xaa | Xaa | Xaa | Xaa 240 |
| Xaa | Xaa | Xaa | Xaa | Xaa 245 | Xaa | Xaa | Xaa | Xaa | Xaa 250 | Xaa | Xaa | Xaa | Xaa | Xaa 255 |
| Xaa | Xaa | Xaa | Xaa 260 | Xaa | Xaa | Xaa | Xaa | Xaa 265 | Xaa | Xaa | Xaa | Xaa | Xaa 270 | Xaa |
| Xaa | Xaa | Xaa | Xaa 275 | Xaa | Xaa | Xaa | Xaa | Xaa 280 | Xaa | Xaa | Xaa | Xaa | Xaa 285 | Xaa | Xaa |
| Xaa | Xaa | Xaa 290 | Xaa | Xaa | Xaa | Xaa | Xaa 295 | Xaa | Xaa | Xaa | Xaa | Xaa 300 | Xaa | Xaa |
| Xaa 305 | Xaa | Xaa | Xaa | Xaa | Xaa 310 | Xaa | Xaa | Xaa | Xaa | Xaa 315 | Xaa | Xaa | Xaa | Xaa | Xaa 320 |
| Xaa | Xaa | Xaa | Xaa | Xaa 325 | Xaa | Xaa | Xaa | Xaa | Xaa 330 | Xaa | Xaa | Xaa | Xaa | Xaa 335 |
| Xaa | Xaa | Xaa | Xaa 340 | Xaa | Xaa | Xaa | Xaa | Xaa 345 | Xaa | Xaa | Xaa | Xaa | Xaa 350 | Xaa |
| Xaa | Xaa | Xaa | Xaa 355 | Xaa | Xaa | Xaa | Xaa | Xaa 360 | Xaa | Xaa | Xaa | Xaa | Xaa 365 | Xaa | Arg |
| Glu | Lys | Arg 370 | Phe | Thr | Phe | Val | Leu 375 | Ala | Val | Val | Ile | Gly 380 | Val | Phe | Val |
| Val 385 | Cys | Trp | Phe | Pro | Phe 390 | Phe | Thr | Tyr | Thr | Leu 395 | Thr | Ala | Val | Gly 400 |
| Cys | Ser | Val | Pro | Arg 405 | Thr | Leu | Phe | Lys | Phe 410 | Phe | Trp | Phe | Gly | Tyr 415 |
| Cys | Asn | Ser | Ser | Leu | Asn | Pro | Val | Ile | Tyr | Thr | Ile | Phe | Asn | His | Asp |

|   | 420 | 425 | 430 |
|---|---|---|---|

Phe Arg Arg Ala Phe Lys Lys Ile Leu Cys Xaa Xaa Xaa Xaa Xaa
        435                    440                        445

Xaa Xaa
450

( 2 ) INFORMATION FOR SEQ ID NO:12:

( i ) SEQUENCE CHARACTERISTICS:
        ( A ) LENGTH: 421 amino acids
        ( B ) TYPE: amino acid
        ( C ) STRANDEDNESS: Not Relevant
        ( D ) TOPOLOGY: Not Relevant ( i i ) MOLECULE TYPE: protein ( x i ) SEQUENCE DESCRIPTION: SEQ ID NO:12:

Met Asp Val Leu Ser Pro Gly Gly Asn Asn Thr Thr Ser Pro Pro Ala
1               5                   10                  15

Pro Phe Glu Thr Gly Gly Asn Thr Thr Gly Ile Ser Asp Val Thr Val
            20                  25                  30

Ser Tyr Gln Val Ile Thr Ser Leu Leu Leu Gly Thr Leu Ile Phe Cys
        35                  40                  45

Ala Val Leu Gly Asn Ala Cys Val Val Ala Ala Ile Ala Leu Glu Arg
    50                  55                  60

Ser Leu Gln Asn Val Ala Asn Tyr Leu Ile Gly Ser Leu Ala Val Thr
65                  70                  75                  80

Asp Leu Met Val Ser Val Leu Val Leu Pro Met Ala Ala Leu Tyr Gln
                85                  90                  95

Val Leu Asn Lys Trp Thr Leu Gly Gln Val Thr Cys Asp Leu Phe Ile
            100                 105                 110

Ala Leu Asp Val Leu Cys Cys Thr Ser Ser Ile Leu His Leu Cys Ala
        115                 120                 125

Ile Ala Leu Asp Arg Tyr Trp Ala Ile Thr Asp Pro Ile Asp Tyr Val
    130                 135                 140

Asn Lys Arg Thr Pro Arg Pro Arg Ala Leu Thr Ser Leu Thr Trp Leu
145                 150                 155                 160

Ile Gly Phe Leu Ile Ser Ile Pro Pro Met Leu Gly Trp Arg Thr Pro
                165                 170                 175

Glu Asp Arg Ser Asp Pro Asp Ala Cys Thr Ile Ser Lys Asp Met Gly
            180                 185                 190

Tyr Thr Ile Tyr Ser Thr Phe Gly Ala Phe Tyr Ile Pro Leu Leu Leu
        195                 200                 205

Met Leu Val Leu Tyr Gly Arg Ile Phe Arg Ala Ala Arg Phe Arg Ile
    210                 215                 220

Pro Lys Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

|     |     |     |     |     |     |     |     |     |     |     |     |     |     |     |
|-----|-----|-----|-----|-----|-----|-----|-----|-----|-----|-----|-----|-----|-----|-----|
| Xaa | Xaa | Xaa | Xaa | Xaa | Xaa | Xaa | Xaa | Xaa | Xaa | Xaa | Xaa | Xaa | Xaa | Xaa |
|     |     |     |     | 325 |     |     |     |     | 330 |     |     |     |     | 335 |
| Xaa | Arg | Glu | Arg | Lys | Thr | Val | Lys | Thr | Leu | Gly | Ile | Ile | Met | Gly | Thr |
|     |     |     | 340 |     |     |     |     | 345 |     |     |     |     | 350 |     |
| Phe | Ile | Leu | Cys | Trp | Leu | Pro | Phe | Phe | Ile | Val | Ala | Leu | Val | Leu | Pro |
|     |     |     | 355 |     |     |     | 360 |     |     |     |     | 365 |     |     |
| Phe | Cys | Glu | Ser | Ser | Cys | His | Met | Pro | Thr | Leu | Leu | Gly | Ala | Ile | Ile |
|     |     | 370 |     |     |     |     | 375 |     |     |     |     | 380 |     |     |
| Asn | Trp | Leu | Gly | Tyr | Ser | Asn | Ser | Leu | Leu | Asn | Pro | Val | Ile | Tyr | Ala |
| 385 |     |     |     |     | 390 |     |     |     |     | 395 |     |     |     |     | 400 |
| Tyr | Phe | Asn | Lys | Asp | Phe | Gln | Asn | Ala | Phe | Lys | Lys | Ile | Ile | Lys | Cys |
|     |     |     |     | 405 |     |     |     |     | 410 |     |     |     |     | 415 |     |
| Xaa | Xaa | Xaa | Xaa | Xaa |
|     |     |     | 420 |     |

( 2 ) INFORMATION FOR SEQ ID NO:13:

( i ) SEQUENCE CHARACTERISTICS:
        ( A ) LENGTH: 461 amino acids
        ( B ) TYPE: amino acid
        ( C ) STRANDEDNESS: Not Relevant
        ( D ) TOPOLOGY: Not Relevant ( i i ) MOLECULE TYPE: protein ( x i ) SEQUENCE DESCRIPTION: SEQ ID NO:13:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Asn | Thr | Ser | Ala | Pro | Pro | Ala | Val | Ser | Pro | Asn | Ile | Thr | Val | Leu |
| 1   |     |     |     | 5   |     |     |     |     | 10  |     |     |     |     | 15  |     |
| Ala | Pro | Gly | Lys | Gly | Pro | Trp | Gln | Val | Ala | Phe | Ile | Gly | Ile | Thr | Thr |
|     |     |     | 20  |     |     |     |     | 25  |     |     |     |     | 30  |     |     |
| Gly | Leu | Leu | Ser | Leu | Ala | Thr | Val | Thr | Gly | Asn | Leu | Leu | Val | Ile | Ile |
|     |     | 35  |     |     |     |     | 40  |     |     |     |     | 45  |     |     |     |
| Ser | Phe | Lys | Val | Asn | Thr | Glu | Leu | Lys | Thr | Val | Asn | Asn | Tyr | Phe | Leu |
|     | 50  |     |     |     |     | 55  |     |     |     |     | 60  |     |     |     |     |
| Leu | Ser | Leu | Ala | Cys | Ala | Asp | Leu | Ile | Ile | Gly | Thr | Phe | Ser | Met | Asn |
| 65  |     |     |     |     | 70  |     |     |     |     | 75  |     |     |     |     | 80  |
| Leu | Tyr | Thr | Thr | Tyr | Leu | Leu | Met | Gly | His | Trp | Ala | Leu | Gly | Thr | Leu |
|     |     |     |     | 85  |     |     |     |     | 90  |     |     |     |     | 95  |     |
| Ala | Cys | Asp | Leu | Trp | Leu | Ala | Leu | Asp | Tyr | Val | Ala | Ser | Asn | Ala | Ser |
|     |     |     | 100 |     |     |     |     | 105 |     |     |     |     | 110 |     |     |
| Val | Met | Asn | Leu | Leu | Leu | Ile | Ser | Phe | Asp | Arg | Tyr | Phe | Ser | Val | Thr |
|     |     | 115 |     |     |     |     | 120 |     |     |     |     | 125 |     |     |     |
| Arg | Pro | Leu | Ser | Tyr | Arg | Ala | Lys | Arg | Thr | Pro | Arg | Arg | Ala | Ala | Leu |
|     | 130 |     |     |     |     | 135 |     |     |     |     | 140 |     |     |     |     |
| Met | Ile | Gly | Leu | Ala | Trp | Leu | Val | Ser | Phe | Val | Leu | Trp | Ala | Pro | Ala |
| 145 |     |     |     |     | 150 |     |     |     |     | 155 |     |     |     |     | 160 |
| Ile | Leu | Phe | Trp | Gln | Tyr | Leu | Val | Gly | Glu | Arg | Thr | Val | Leu | Ala | Gly |
|     |     |     |     | 165 |     |     |     |     | 170 |     |     |     |     | 175 |     |
| Gln | Cys | Tyr | Ile | Gln | Phe | Leu | Ser | Gln | Pro | Ile | Ile | Thr | Phe | Gly | Thr |
|     |     |     | 180 |     |     |     |     | 185 |     |     |     |     | 190 |     |     |
| Ala | Met | Ala | Ala | Phe | Tyr | Leu | Pro | Val | Thr | Val | Met | Cys | Thr | Leu | Tyr |
|     |     | 195 |     |     |     |     | 200 |     |     |     |     | 205 |     |     |     |
| Trp | Arg | Ile | Tyr | Arg | Glu | Thr | Glu | Asn | Arg | Ala | Arg | Glu | Xaa | Xaa | Xaa |
|     | 210 |     |     |     |     | 215 |     |     |     |     | 220 |     |     |     |     |
| Xaa | Xaa | Xaa | Xaa | Xaa | Xaa | Xaa | Xaa | Xaa | Xaa | Xaa | Xaa | Xaa | Xaa | Xaa | Xaa |
| 225 |     |     |     |     | 230 |     |     |     |     | 235 |     |     |     |     | 240 |

| Xaa | Xaa | Xaa | Xaa | Xaa | Xaa | Xaa | Xaa | Xaa | Xaa | Xaa | Xaa | Xaa | Xaa | Xaa | Xaa |
|-----|-----|-----|-----|-----|-----|-----|-----|-----|-----|-----|-----|-----|-----|-----|-----|
|     |     |     | 245 |     |     |     |     | 250 |     |     |     |     | 255 |     |     |
| Xaa | Xaa | Xaa | Xaa | Xaa | Xaa | Xaa | Xaa | Xaa | Xaa | Xaa | Xaa | Xaa | Xaa | Xaa | |
|     |     |     | 260 |     |     |     |     | 265 |     |     |     |     | 270 |     | |
| Xaa | Xaa | Xaa | Xaa | Xaa | Xaa | Xaa | Xaa | Xaa | Xaa | Xaa | Xaa | Xaa | Xaa | Xaa | |
|     |     | 275 |     |     |     |     | 280 |     |     |     |     | 285 |     |     | |
| Xaa | Xaa | Xaa | Xaa | Xaa | Xaa | Xaa | Xaa | Xaa | Xaa | Xaa | Xaa | Xaa | Xaa | Xaa | |
|     | 290 |     |     |     |     | 295 |     |     |     |     | 300 |     |     |     | |
| Xaa | Xaa | Xaa | Xaa | Xaa | Xaa | Xaa | Xaa | Xaa | Xaa | Xaa | Xaa | Xaa | Xaa | Xaa | |
| 305 |     |     |     |     | 310 |     |     |     |     | 315 |     |     |     | 320 | |
| Xaa | Xaa | Xaa | Xaa | Xaa | Xaa | Xaa | Xaa | Xaa | Xaa | Xaa | Xaa | Xaa | Xaa | Xaa | |
|     |     |     |     | 325 |     |     |     |     | 330 |     |     |     |     | 335 | |
| Xaa | Xaa | Xaa | Xaa | Xaa | Xaa | Xaa | Xaa | Xaa | Xaa | Xaa | Xaa | Xaa | Xaa | Xaa | |
|     |     |     | 340 |     |     |     |     | 345 |     |     |     |     | 350 |     | |
| Xaa | Xaa | Xaa | Xaa | Xaa | Xaa | Xaa | Lys | Glu | Lys | Lys | Ala | Ala | Arg | Thr | Leu |
|     |     | 355 |     |     |     |     | 360 |     |     |     |     | 365 |     |     |     |
| Ser | Ala | Ile | Leu | Leu | Ala | Phe | Ile | Val | Thr | Trp | Thr | Pro | Tyr | Asn | Ile |
|     | 370 |     |     |     |     | 375 |     |     |     |     | 380 |     |     |     |     |
| Met | Val | Leu | Val | Ser | Thr | Phe | Cys | Lys | Asp | Cys | Val | Pro | Glu | Thr | Leu |
| 385 |     |     |     |     | 390 |     |     |     |     | 395 |     |     |     |     | 400 |
| Trp | Glu | Leu | Gly | Tyr | Trp | Leu | Cys | Tyr | Val | Asn | Ser | Thr | Ile | Asn | Pro |
|     |     |     |     | 405 |     |     |     |     | 410 |     |     |     |     | 415 |     |
| Met | Cys | Tyr | Ala | Leu | Cys | Asn | Lys | Ala | Phe | Arg | Asp | Thr | Phe | Arg | Leu |
|     |     |     | 420 |     |     |     |     | 425 |     |     |     |     | 430 |     |     |
| Leu | Leu | Leu | Cys | Xaa | Xaa | Xaa | Xaa | Xaa | Xaa | Xaa | Xaa | Xaa | Xaa | Xaa | Xaa |
|     |     | 435 |     |     |     |     | 440 |     |     |     |     | 445 |     |     |     |
| Xaa | Xaa | Xaa | Xaa | Xaa | Xaa | Xaa | Xaa | Xaa | Xaa | Xaa | Xaa | Xaa | | | |
|     | 450 |     |     |     |     | 455 |     |     |     |     | 460 |     | | | |

( 2 ) INFORMATION FOR SEQ ID NO:14:

( i ) SEQUENCE CHARACTERISTICS:
        ( A ) LENGTH: 387 amino acids
        ( B ) TYPE: amino acid
        ( C ) STRANDEDNESS: Not Relevant
        ( D ) TOPOLOGY: Not Relevant ( i i ) MOLECULE TYPE: protein ( x i ) SEQUENCE DESCRIPTION: SEQ ID NO:14:

| Met | Gly | Ala | Cys | Val | Val | Met | Thr | Asp | Ile | Asn | Ile | Ser | Ser | Gly | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asp | Ser | Asn | Ala | Thr | Gly | Ile | Thr | Ala | Phe | Ser | Met | Pro | Gly | Trp | Gln |
|     |     |     | 20  |     |     |     |     | 25  |     |     |     |     | 30  |     |     |
| Leu | Ala | Leu | Trp | Thr | Ala | Ala | Tyr | Leu | Ala | Leu | Val | Leu | Val | Ala | Val |
|     |     | 35  |     |     |     |     | 40  |     |     |     |     | 45  |     |     |     |
| Met | Gly | Asn | Ala | Thr | Val | Ile | Trp | Ile | Ile | Leu | Ala | His | Gln | Arg | Met |
|     | 50  |     |     |     |     | 55  |     |     |     |     | 60  |     |     |     |     |
| Arg | Thr | Val | Thr | Asn | Tyr | Phe | Ile | Val | Asn | Leu | Ala | Leu | Ala | Asp | Leu |
| 65  |     |     |     |     | 70  |     |     |     |     | 75  |     |     |     |     | 80  |
| Cys | Met | Ala | Ala | Phe | Asn | Ala | Ala | Phe | Asn | Phe | Val | Tyr | Ala | Ser | His |
|     |     |     |     | 85  |     |     |     |     | 90  |     |     |     |     | 95  |     |
| Asn | Ile | Trp | Tyr | Phe | Gly | Arg | Ala | Phe | Cys | Tyr | Phe | Gln | Asn | Leu | Phe |
|     |     |     | 100 |     |     |     |     | 105 |     |     |     |     | 110 |     |     |
| Pro | Ile | Thr | Ala | Met | Phe | Val | Ser | Ile | Tyr | Ser | Met | Thr | Ala | Ile | Ala |
|     |     | 115 |     |     |     |     | 120 |     |     |     |     | 125 |     |     |     |
| Ala | Asp | Arg | Tyr | Met | Ala | Ile | Val | His | Pro | Phe | Gln | Pro | Arg | Leu | Ser |

```
                    130                               135                               140
Ala  Pro  Gly  Thr  Arg  Ala  Val  Ile  Ala  Gly  Ile  Trp  Leu  Val  Ala  Leu
145                      150                      155                           160

Ala  Leu  Ala  Phe  Pro  Gln  Cys  Phe  Tyr  Ser  Thr  Ile  Thr  Thr  Asp  Glu
                    165                      170                     175

Gly  Ala  Thr  Lys  Cys  Val  Val  Ala  Trp  Pro  Glu  Asp  Ser  Gly  Gly  Lys
                    180                      185                     190

Met  Leu  Leu  Leu  Tyr  His  Leu  Ile  Val  Ile  Ala  Leu  Ile  Tyr  Phe  Leu
               195                      200                     205

Pro  Leu  Val  Val  Met  Phe  Val  Ala  Tyr  Ser  Val  Ile  Gly  Leu  Thr  Leu
          210                      215                     220

Trp  Arg  Arg  Ser  Val  Pro  Xaa  Xaa  Xaa  Xaa  Xaa  Xaa  Xaa  Xaa  Xaa  Xaa
225                      230                     235                           240

Xaa  Xaa  Xaa  Ala  Lys  Lys  Lys  Phe  Val  Lys  Thr  Met  Val  Leu  Val  Val
                    245                      250                          255

Val  Thr  Phe  Ala  Ile  Cys  Trp  Leu  Pro  Tyr  His  Leu  Tyr  Phe  Ile  Leu
               260                      265                     270

Gly  Thr  Phe  Gln  Glu  Asp  Ile  Tyr  Cys  His  Lys  Phe  Ile  Gln  Gln  Val
          275                      280                     285

Tyr  Leu  Ala  Leu  Phe  Trp  Leu  Ala  Met  Ser  Ser  Thr  Met  Tyr  Asn  Pro
     290                      295                     300

Ile  Ile  Tyr  Cys  Cys  Leu  Asn  His  Arg  Phe  Arg  Ser  Gly  Phe  Arg  Leu
305                      310                     315                           320

Ala  Phe  Arg  Cys  Xaa  Xaa  Xaa  Xaa  Xaa  Xaa  Xaa  Xaa  Xaa  Xaa  Xaa  Xaa
                    325                      330                          335

Xaa  Xaa  Xaa  Xaa  Xaa  Xaa  Xaa  Xaa  Xaa  Xaa  Xaa  Xaa  Xaa  Xaa  Xaa  Xaa
               340                      345                     350

Xaa  Xaa  Xaa  Xaa  Xaa  Xaa  Xaa  Xaa  Xaa  Xaa  Xaa  Xaa  Xaa  Xaa  Xaa  Xaa
          355                      360                     365

Xaa  Xaa  Xaa  Xaa  Xaa  Xaa  Xaa  Xaa  Xaa  Xaa  Xaa  Xaa  Xaa  Xaa  Xaa  Xaa
     370                      375                     380

Xaa  Xaa  Xaa
385
```